(12) United States Patent
Forssmann et al.

(10) Patent No.: US 9,045,563 B2
(45) Date of Patent: Jun. 2, 2015

(54) CXC CHEMOKINE RECEPTOR 4 (CXCR4) ANTAGONISTIC POLYPEPTIDE

(75) Inventors: Wolf-Georg Forssmann, Wles-Wambach (DE); Frank Kirchhoff, Ulm (DE); Jan Münch, Neu-Ulm (DE); Ludger Ständker, Hannover (DE)

(73) Assignee: PHARIS BIOTECH GMBH, Hannover (DE)

( * ) Notice: Subject to any disclaimer, the term of this patent is extended or adjusted under 35 U.S.C. 154(b) by 1342 days.

(21) Appl. No.: 12/452,480

(22) PCT Filed: Jul. 3, 2008

(86) PCT No.: PCT/EP2008/058566
§ 371 (c)(1),
(2), (4) Date: Apr. 5, 2010

(87) PCT Pub. No.: WO2009/004054
PCT Pub. Date: Jan. 8, 2009

(65) Prior Publication Data
US 2013/0029902 A1 Jan. 31, 2013

(30) Foreign Application Priority Data

Jul. 3, 2007 (DE) .......................... 10 2007 030 904

(51) Int. Cl.
*C07K 14/435* (2006.01)
*C07K 14/765* (2006.01)
*A61K 38/00* (2006.01)

(52) U.S. Cl.
CPC ............... *C07K 14/765* (2013.01); *A61K 38/00* (2013.01); *G01N 2333/715* (2013.01)

(58) Field of Classification Search
None
See application file for complete search history.

(56) References Cited

U.S. PATENT DOCUMENTS 6,849,593 B1 * 2/2005 Forssmann et al. ............ 514/2.4
2005/0255115 A1 * 11/2005 Huang et al. ............... 424/155.1

FOREIGN PATENT DOCUMENTS

WO WO2007097923 A2 * 8/2007

OTHER PUBLICATIONS

Li et al., "Matrix-assisted laser desorption/ionization time-of-flight mass spectrometry assay for organophosphorus toxicants bound to human albumin at Tyr411," Analytical Biochem. 361:263-272 (2006).*
Li et al., "Matrix-assisted laser desorption/ionization time-of-flight mass spectrometry assay for organophosphorus toxicants bound to human albumin at Tyr411," Anal Biochem. 361:263-272 (Feb. 2007).*
Li et al., "Matrix-assisted laser desorption/ionization time-of-flight mass spectrometry assay for organophosphorus toxicants bound to human albumin at Tyr411," 361:263-272 (Feb. 2007)—copy provided in OA mailed Feb. 25, 2013.*
Uniprot Accession No. Q5KTJ5, accessed Jun. 13, 2014 at URL: uniprot.org/uniprot/Q5KTJ5.*
Uniprot Accession No. P08835, accessed Jun. 13, 2014 at URL: uniprot.org/uniprot/P08835.*
Uniprot Accession No. A5PC28, accessed Jun. 13, 2014 at URL: uniprot.org/uniprot/A5PC28.*
Li et al. "Matrix-assisted laser desorption/ionization time-of-flight mass spectrometry assay for organophosporus toxicants bound to human albumin at Tyr411." Analytical Biochemistry, vol. 361, No. 2, Jan. 24, 2007, pp. 263-272.
Schulz-Knappe et al. "Peptide bank generated by large-scale preparation of circulating human peptides" Journal of Chromatography, vol. 776, No. 1, Jul. 25, 1997, pp. 125-132.
Kazmierski Wieslaw M et al. "Peptide, peptidomimetic and small-molecule drug discovery targeting HIV-1 host-cell attachment and entry through gp120, gp41, CCR5 and CXCR4." Chemical Biology and Drug Design, vol. 67, No. 1, Jan. 2006, pp. 13-26.

* cited by examiner

*Primary Examiner* — Julie Ha
*Assistant Examiner* — Kristina M Hellman
(74) *Attorney, Agent, or Firm* — Jacobson Holman PLLC

(57) ABSTRACT

A peptide having the following amino acid sequence:

$$Z_1\text{-LVRYTKKVPQVSTPTL-}Z_2 \text{ (ALB-408)}$$

and its biologically active fragments and/or variants and/or derivatives, especially amidated, acetylated, sulfated, phosphorylated and/or glycosylated derivatives, and peptides obtainable by multiple synthesis which have the biological activity of ALB408-423;
wherein Z represents number of from 0 to 10 amino acid residues.

9 Claims, 15 Drawing Sheets

Fig.1C
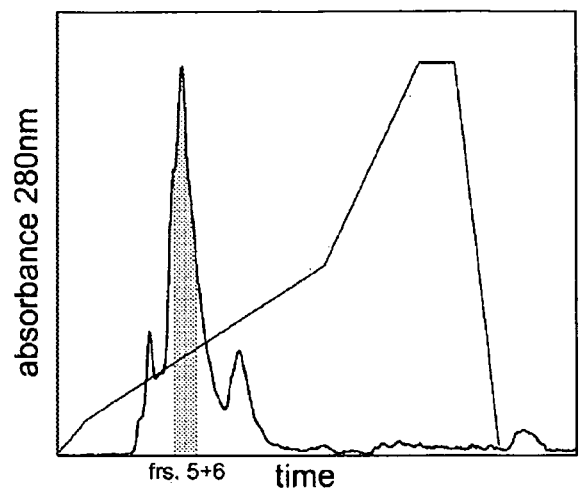
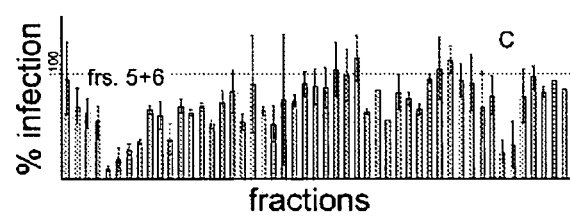
Fig.1D
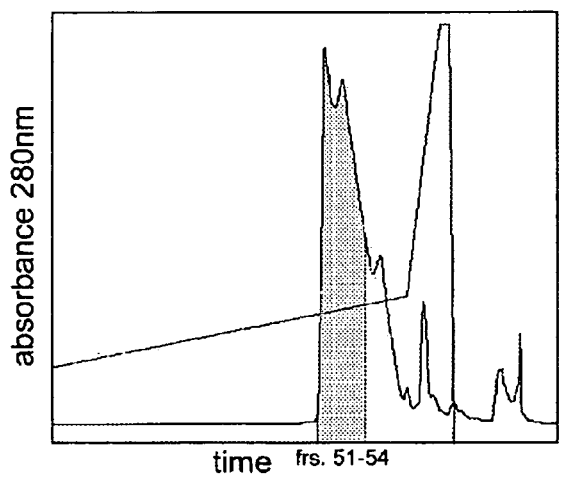
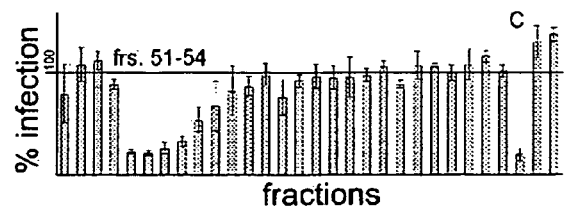

Fig.1E
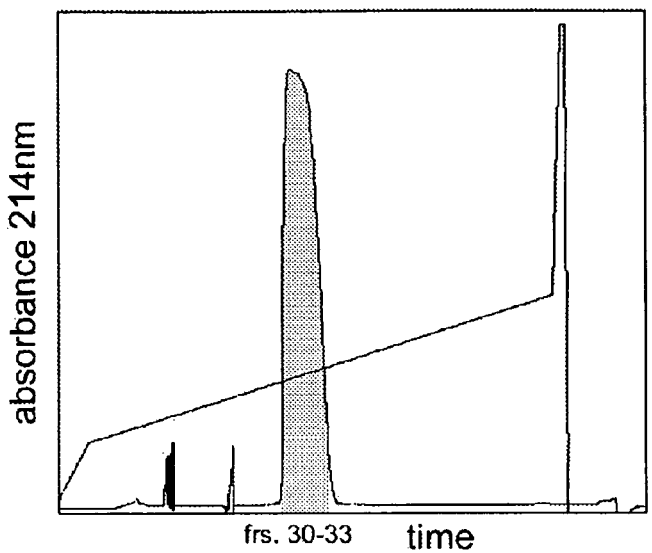
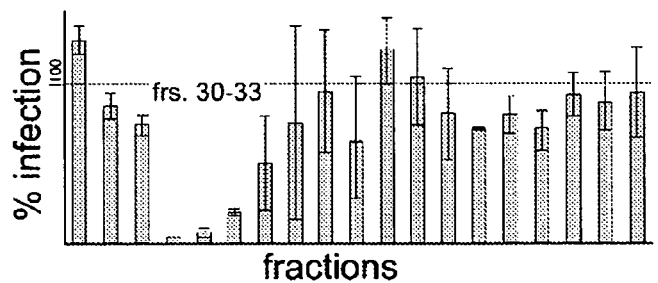
Fig.1F
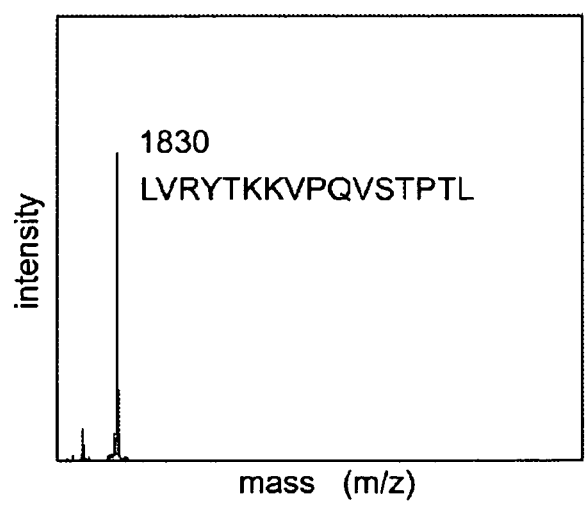

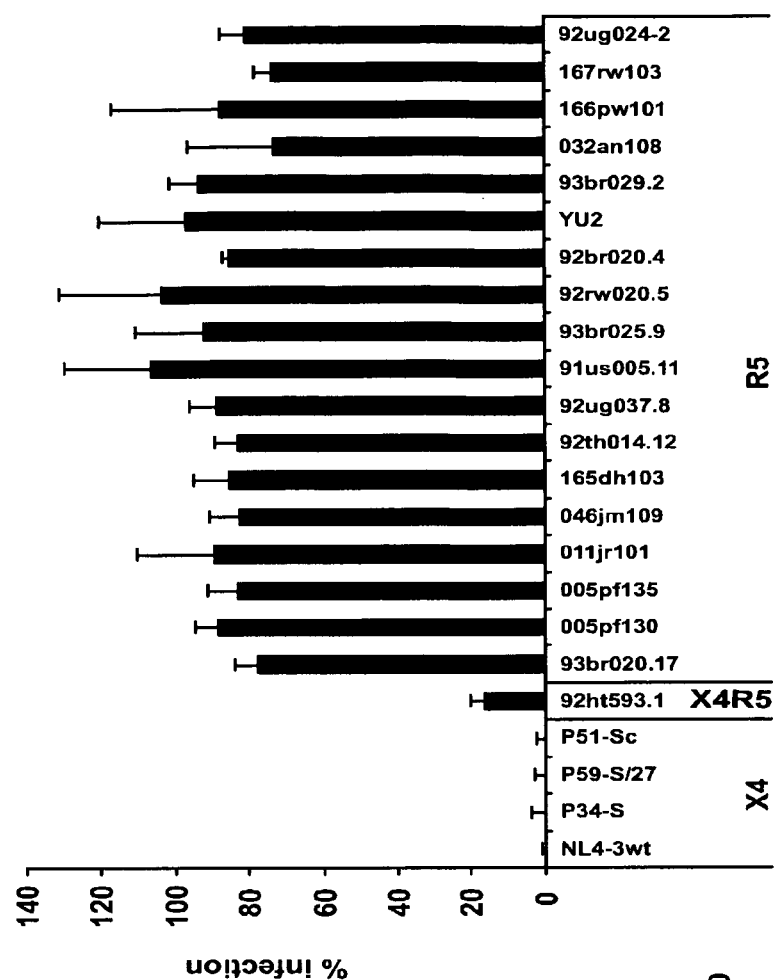
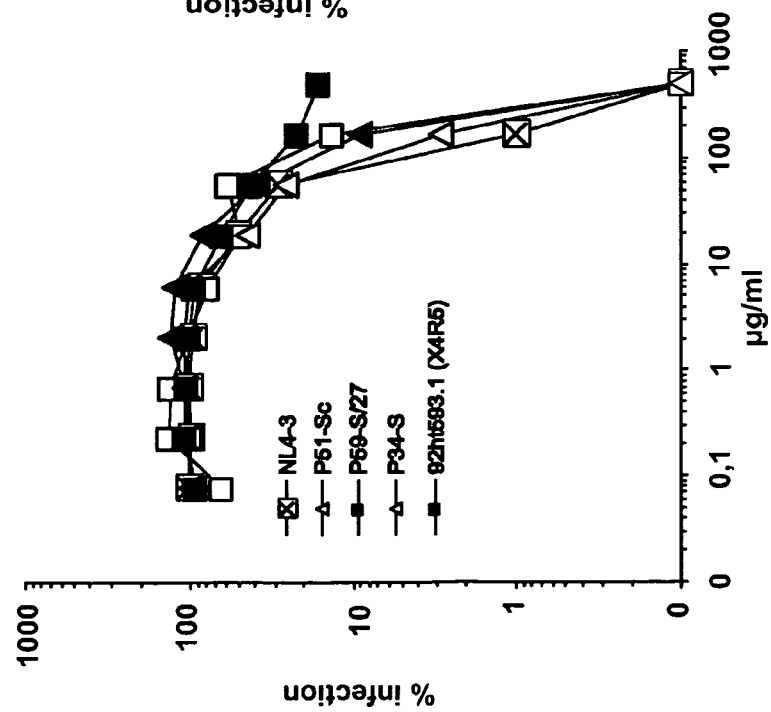
Fig. 3A
Fig. 3B

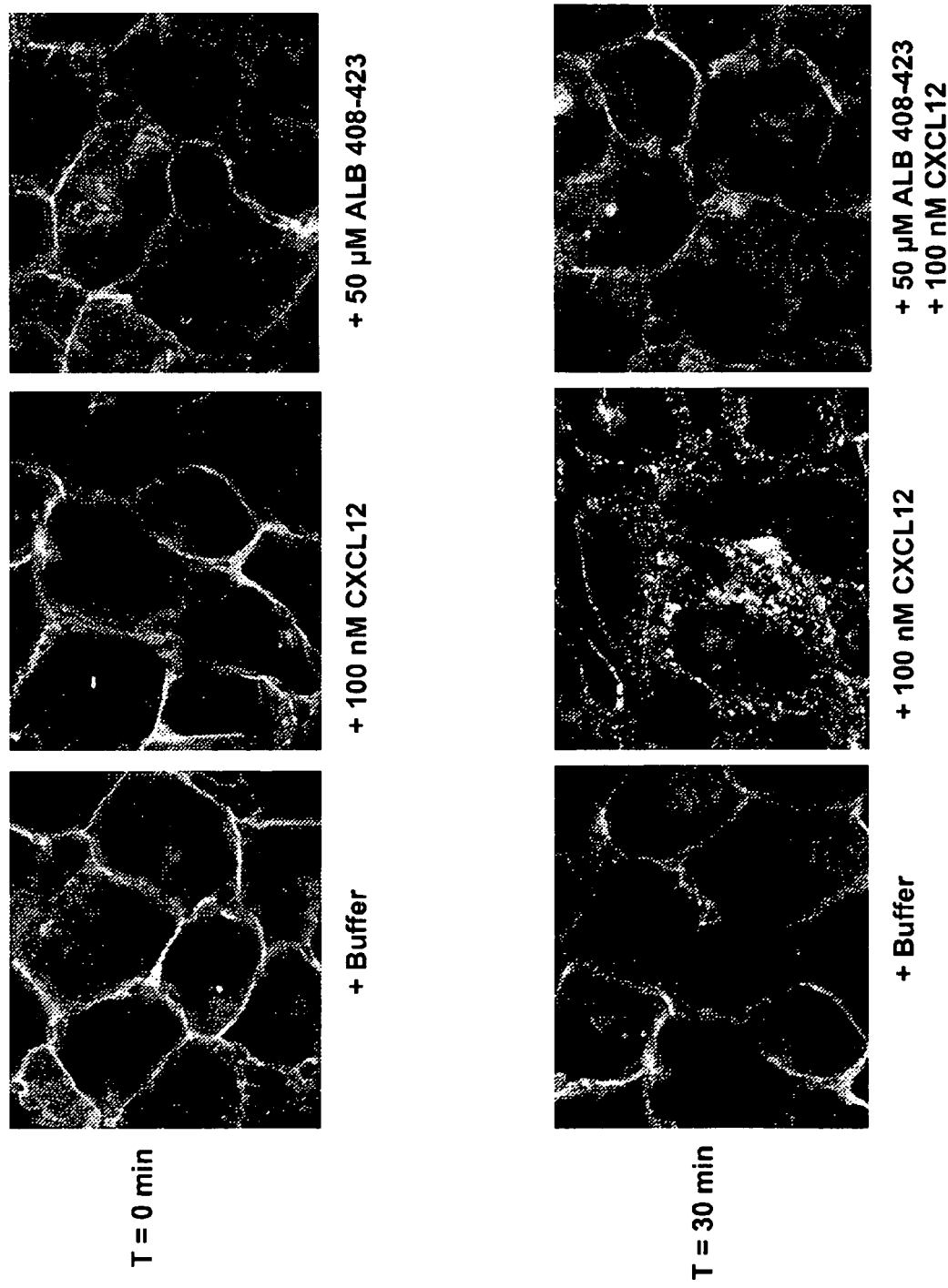

CXC CHEMOKINE RECEPTOR 4 (CXCR4) ANTAGONISTIC POLYPEPTIDE

This is a national stage of PCT/EP08/058566 filed Jul. 3, 2008 and published in English, which has a priority of German no. 10 2007 030 904.1 filed Jul. 3, 2007, hereby incorporated by reference.

FIELD OF THE INVENTION

The present invention relates to a CXC chemokine receptor 4 (CXCR4) antagonistic polypeptide (protein) that inhibits infection of CXCR4 depending viruses such as HIV-1 and blocks tumor cell migration mediated by CXCL12 binding to CXCR4: Human circulating antiviral albumin fragment (ALB408-423) and its therapeutic and diagnostic use. The invention includes the naturally occurring form of ALB408-423 and fragments derived therefrom and/or analogues or derivatives, and finally a medicament containing said natural, recombinant and synthetic peptides to be used for medicinal indications and to be used as a diagnostic agent. In addition, the invention includes modified forms and derivatives of ALB408-423 that have a particularly favorable therapeutic effectiveness. Further, it includes a nucleic acid probe hybridizing to ALB408-423 or one of its fragments and/or derivatives, and antibodies or antagonists directed against ALB408-423 or one of its fragments and/or derivatives, for diagnostic or therapeutic purposes, especially in viral diseases for the treatment of HIV-1 and HIV-2 infections as well as for the treatment of neoplastic diseases to prevent cancer cell metastasis or for the treatment of chronic inflammatory diseases such as asthma, pulmonary fibrosis or rheumatoid arthritis

BACKGROUND OF THE INVENTION

Chemokine receptors are expressed on the surface of certain cells, which interact with cytokines called chemokines. The CXC chemokine receptor 4 (CXCR4) is a G-protein-coupled receptor that transduces signals of its endogenous ligand, the chemokine CXCL12 (stromal cell-derived factor-1, SDF-1). Following interaction of CXCR4/CXCL12 intracellular calcium ($Ca^{2+}$) ions fluxes are triggered. This causes cellular responses, including chemotaxis allowing cells to travel within the organism. CXCR4 is expressed on myeloid cells, T-lymphocytes, B-lymphocytes, epithelial cells, endothelial cells and dendritic cells. The chemokine CXCL12 is the only known agonistic ligand of CXCR4. The interaction between CXCL12 and CXCR4 plays a crucial role in the migration of progenitor cells during embryologic development of the cardiovascular, hemopoietic or central nervous systems. This interaction is also known to be involved in several diseases such as HIV infection/AIDS, cancer cell metastasis, leukemia cell progression, pulmonary fibrosis and rheumatoid arthritis. It is assumed that this interaction may be a critical therapeutic target in all of these diseases. Substances interfering with CXCR4/CXCL12 signaling are assumed to have drug potential, e.g. in HIV/AIDS therapy, or to prevent cell migration processes involved in cancer metastasis, leukemia, and inflammatory diseases such as pulmonary fibrosis, rheumatoid arthritis or asthma (reviewed in Tsutsumi et al., 2007, Peptide Science 88: 279-289). In contrast to receptor agonists such as CXCL12 that induce cellular responses, receptor antagonists are ligands or drugs that do not induce a biological response, i.e. cell migration or $Ca^{2+}$ signaling, upon binding to their receptor. Receptor antagonists are useful drugs already in clinical use (e.g. angiotensin antagonists, β-adrenergic antagonists, serotonergic antagonist or CCR5 antagonists) that can block HIV-1 infection (CCR5 antagonist) or decrease agonist mediated cellular responses. Interaction of receptor antagonists with the receptor inhibits the function of an agonist. Most drug antagonists achieve their potency by competing with endogenous ligands or substrates at structurally defined binding sites on receptors.

It has already been shown in vitro and in vivo that CXCR4 antagonists block cancer cell migration and hence metastasis. CXCR4 is expressed on the surface of a variety of cells (myeloid cells, T-lymphocytes, B-lymphocytes, epithelial cells, endothelial cells and dendritic cells) as well as in 23 different types of cancer cells. CXCL12-CXCR4 interaction is involved in metastasis of several types of cancer, including cancer of the breast, kidney, prostate, lung, and pancreas, and melanoma, neuroblastoma, non-Hodgkin's lymphoma, multiple myeloma, ovarian cancer, and malignant brain tumors (reviewed in Tsutsumi et al., 2007, Peptide Science 88: 279-289). It has been shown that CXCR4 antagonists such as T140 analogous suppress CXCL12 induced pancreatic cell migration and invasion or breast carcinoma cell migration in vitro and in vivo (reviewed in Tsutsumi et al., 2007, Peptide Science 88: 279-289). It has also been demonstrated that CXCR4 antagonists effectively suppress invasion and adhesion of small cell lung cancer (SCLC) in vitro (reviewed in Tsutsumi et al., 2007, Peptide Science 88: 279-289), confirming the involvement of the CXCL12-CXCR4 interaction in SCLC metastasis. CXCR4/CXCL12 interaction is also involved in the development of precursor-B (pre-B) acute lymphoblastic leukemia (ALL) and chronic lymphocytic leukemia (CLL). CXCR4 antagonists also attenuate migration of pre-B ALL cells (reviewed in Tsutsumi et al., 2007, Peptide Science 88: 279-289). Furthermore it has been shown that rheumatoid arthritis is caused by CXCR4 expressing CD4+ memory T cell accumulation in the inflamed synovium. CXCL12 concentration in the synovium of rheumatoid arthritis patients are highly elevated thereby attracting memory T cell. CXCR4 antagonistic molecules block migration of memory T cells into the synovium (reviewed in Tsutsumi et al., 2007, Peptide Science 88: 279-289).

CXCR4 antagonists do not only inhibit binding of the agonist CXCL12 to CXCR4 but also prevent interaction of the HIV glycoprotein gp120 with CXCR4 thereby inhibiting virus infection. The human immunodeficiency viruses 1 and 2 (HIV-1 and HIV-2) use cell surface expressed CD4 as primary receptor and the chemokine receptors CCR5 or CXCR4 as coreceptors for cell entry. Viruses that infect cells via CD4 and CXCR4 are termed CXCR4 (X4) tropic, HIV-1 variants using CD4 and CCR5 as R5 tropic, and those that can use both coreceptors as dualtropic. X4 tropic HIV-1 variants can only be found in about 50% of all AIDS patients whereas R5 tropic HIV variants predominate in earlier stages and the asymptomatic phase of HIV-1 infection. It has been shown that X4 tropic HIV-1 infection can be blocked in vitro and in HIV-1 infected humans by treating cells or patients with CXCR4 antagonists such as AMD3100. Interestingly, Maraviroc, a CCR5 antagonist, is the first clinical approved drug in AIDS therapy that blocks infection of R5 tropic HIV-1 variants (reviewed by Tsibris and Kuritzkes, 2007, Annual Review of Medicine 58:445-459).

Thus, the chemokine receptor CXCR4 is an attractive therapeutic target for the treatment of HIV/AIDS, cancer associated pathologies and chronic inflammatory diseases like asthma or pulmonary fibrosis. CXCR4 antagonists blocking CXCL12 mediated cellular responses could inhibit these important pathways of disease development and progression.

SUMMARY OF THE INVENTION

The invention pertains to a peptide having the following amino acid sequence:

$Z_1$-LVRYTKKVPQVSTPTL-$Z_2$(ALB-408)     (SEQ ID NO: 8)

and its biologically active derivatives, especially amidated, acetylated, sulfated, phosphorylated and/or glycosylated derivatives, and peptides obtainable by multiple synthesis which have the biological activity of ALB408-423;
wherein Z represents a number of from 0 to 10 amino acid residues.

The peptide of the present invention is also related to the peptides of the invention, in particular ALB408-423 peptide according the invention, wherein single or several amino acid residues in the sequence have been exchanged, deleted or added, or chemical modifications on single amino acids of the peptides of the invention, in particular ALB408-423 have been introduced which have similar or the same biological or pharmacological activity of the peptides of the invention, in particular ALB408-423. In particular those peptides are concerned which can easily be obtained by exchanging amino acids of the sequence in a conservative manner which means to exchange hydrophobic amino acids against hydrophobic ones or aromatic against other aromatic amino acids or basic amino acids against other basic amino acids and the like. This is well known to skilled person.

Also retro-inverso peptides of the peptides of the invention are in the scope of the present invention, as well as other derivatives stabilizing the peptide bond against peptidases.

The term derivative means all length fragments including truncations at the N and C terminus, ALB408-423 containing amino acid residue substitutions including D-amino acid residues and modified amino acid residues as well as peptides containing disulfide bonds and extension at the N and C terminus.

Another subject matter of the present invention are polynucleotides coding for the peptides of the invention, in particular ALB408-423 and/or its derivatives. The polynucleotides of the invention are characterized by being constituted of DNA, RNA, genomic DNA or PNA. Polynucleotides coding for the peptides of the invention shall be used for recombinant peptide expression in pro- or eukaryotic cells, mutagenesis studies, cloning in vectors of interest, in particular those that can be used for gene transfer approaches.

A further subject of the present invention is a vector containing the polynucleotides according to the invention. Vectors encoding polynucleotide sequences coding for the peptides of the invention shall be used for recombinant peptide expression in pro- or eukaryotic cells, mutagenesis studies, and particular for ALB408-423 gene transfer into eukaryotic cells.

Another subject of the present invention is a genetically engineered host cell containing the vector according to the invention. A genetically engineered ALB408-423 or related derivative expressing transgenic cell can be used for gene therapy approaches allowing expression and secretion of ALB408-423 and related derivatives in individuals being in the need of CXCR4 antagonists, in particular cancer and AIDS patients.

Yet another subject of the invention is an antibody directed against the polypeptides according to the invention. Those antibodies are useful to detect ALB408-423 and related peptides in body samples like blood, serum, plasma in ELISA, RIA or immune fluorescence for diagnostic purposes.

The peptides of the invention can be administered in a method for the treatment of patients in need of the peptides of the invention, in particular ALB408-423.

A further subject of the present invention is a method for the treatment of patients in need of ALB408-423 inhibition by administering therapeutic amounts of an antagonist/inhibitor the peptides of the invention. ALB408-423 and its derivatives are CXCR4 antagonists allowing to treat several diseases such as HIV infection/AIDS, cancer cell metastasis, leukemia cell progression, pulmonary fibrosis and rheumatoid arthritis and other cancer and inflammatory diseases.

A galenic formulation consisting of polypeptides of the invention is also subject matter of the invention.

According to the invention also a method is provided for the treatment of patients wherein a therapeutical effect of the polypeptide is achieved by administering DNA coding for the peptides of the invention and its in vivo expression in the patient.

The peptide of the invention can be provided by a process comprising an extraction from hemofiltrate by cation-exchange extraction followed by elution of adsorbed substances, renewed cation-exchange chromatography of the extract containing the peptides, and fractional reverse-phase chromatography.

Alternatively, the process for the manufacturing of the peptides according to the invention can be performed by solid-phase synthesis in terms of a Merrifield synthesis or liquid-phase synthesis by methods known per se to the skilled person using protected amino acids, and its purification.

A further process for the manufacturing of the peptides according to the invention employs methods of heterologous expression known to the skilled person using common biotechnological vectors.

Also a subject of the present invention is a diagnostic agent containing a poly- or monoclonal antibody of the invention or containing the nucleic acid or mRNA coding for the peptides of the invention, in particular ALB408-423.

The diagnostic agent of the invention contains the peptides, or polynucleotides of the invention for use in test systems for assaying levels of this substance in samples such as tissue, plasma, urine and cerebrospinal fluid.

In particular the diagnostic agents and test systems detecting the peptides of the invention are used for assaying tissue, plasma, urine and cerebrospinal fluid levels of this substance by means of mass-spectrometric methods, such as MALDI-MS or ESI-MS, in connection with sample preparation by RP-HPLC, protein precipitation and/or solid-phase extraction.

Subject of the invention is also a diagnostic agent containing the peptides of the invention as markers for viral diseases, bacterial and fungal infections, inflammatory and neoplastic processes, and as markers in inflammatory processes, disturbed inflammation reactions, tumor diseases, growth disorders, diseases of the immune system, and as markers in bone diseases.

The present invention provides also a medicament containing the peptides of the invention as an active ingredient of galenic forms for oral, intravenous, intramuscular, intracutaneous, subcutaneous, intrathecal administration, and as an aerosol for transpulmonary administration.

The peptides, the polynucleotides, the antibodies/antagonists, and the galenic formulation according to the invention can be used for the treatment of viral diseases, especially HIV-1, HIV-2, cytomegalovirus, herpes simplex virus (types 1 and 2), varicella zoster virus, hepatitis A and hepatitis B viruses, influenza virus, polio virus, rhinovirus, rubella virus, measles virus, rabies virus, Rous sarcoma virus, Epstein-Barr virus, and for the treatment of bacterial and fungal infections, inflammatory processes, disturbed inflammation reactions, tumor diseases, growth disorders, neuronal diseases, diseases of blood clotting and hematopoiesis, vascular diseases, diseases of the immune system, and for wound and bone healing.

The invention is described in more detail using ALB408-423 as specific example. It is readily understood that likewise the peptides of the invention can replace ALB408-423 in the following descriptions.

DETAILED DESCRIPTION OF THE INVENTION

FIG. 1A-F show details of the isolation of ALB408-423 from human hemofiltrate.

FIG. 3 shows chemically synthesized ALB408-423 specifically blocks X4 tropic HIV-1 infection.

FIG. 15 shows ALB408-423 blocks CXCL12 mediated CXCR4 internalization.

Figure 1A:
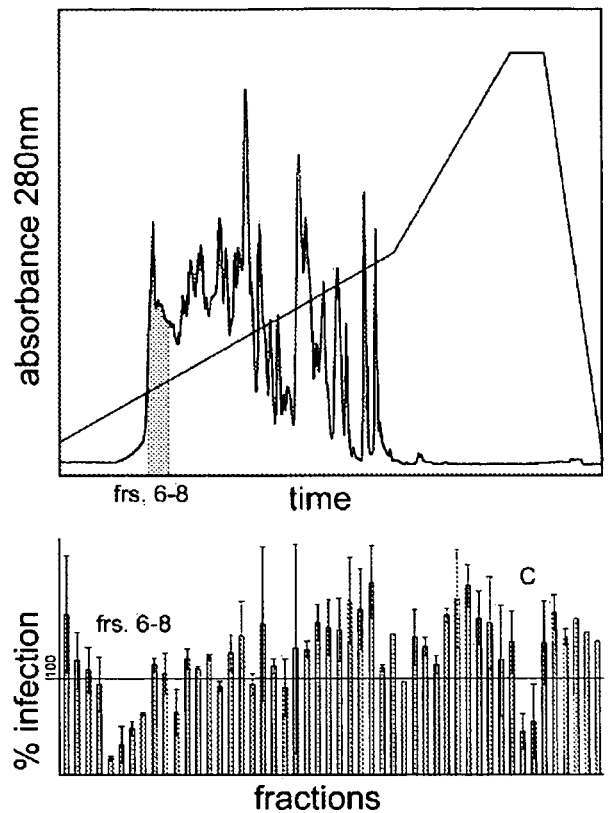

ALB408-423 could be surprisingly isolated from human hemofiltrate by means of chromatographical methods and a biological assay. The biochemical characterization of the peptide according to the invention was effected by mass spectrometry including a complete sequence analysis of the amino acids.

The peptide has the following amino acid sequence Seq ID No 8:

LVRYTKKVPQVSTPTL

The molecular weight of the peptide ALB408-423 according to the invention is: 1830.2 Da The isoelectric point (pI) of the peptide ALB408-423 according to the invention is 10.3.

Surprisingly, the peptide according to the invention is a fragment comprising 16 amino acids of the known human plasma protein serum albumin (Accession No. NP000468), which consists of 585 amino acids in its processed form. Human albumin is a soluble monomeric serum protein having a molecular weight of about 65,000 that accounts for more than half the total plasma protein (concentration: 3.5 to 5 g/dl). The function of human albumin is predominantly described as a carrier molecule for all kinds of hydrophobic as well as hydrophilic substances, e.g., steroid and peptide hormones, fatty acids, vitamins, pharmaceuticals and cations. Due to its very high serum concentration, it contributes substantially to the stabilization of the blood pH, the extracellular liquid volume and the maintenance of colloid-osmotic pressure. Albumin has a globular structure stabilized by a high number of disulfide bridges and is usually not glycosylated, but alterations due to acetylation, enzymatic glycosylation and non-enzymatic glycosylation occur frequently in the course of molecular ageing or upon pathophysiological changes. It is synthesized by the liver as pre-pro-albumin having 609 amino acids; the N-terminal signal peptide comprising 18 amino acids is cleaved of intracellularly upon entry in the endoplasmic reticulum; another 6 amino acids is removed in the Golgi apparatus before the mature albumin comprising 585 amino acids is secreted by the liver cells. The clearance of albumin takes place through the kidney, the gastrointestinal tract and in the tissue cells of the liver.

The peptide sequence of ALB408-423 according to the invention starts with amino acid 408 and thus comprises the amino acids 408 to 423 of the circulating form of albumin. It is evidently produced by natural processing of the albumin precursor by corresponding proteases.

Surprisingly, the peptide according to the invention is an antagonist for the CXC chemokine receptor 4 (CXCR4) and causes a suppression of HIV-1 infection and replication in human cells as well as a suppression of CXCL12/CXCR4 induced cellular responses such as cell migration, $Ca^{2+}$ mobilization or CXCR4 internalization.

The peptide according to the invention is obtainable by chromatographic purification from human hemofiltrate (HF). HF is obtained in large amounts during ultrafiltration of the blood of kidney patients (example 1). HF contains all peptides and proteins circulating in human blood with a molecular weight below 30 kDa. Peptides and proteins in HF were extracted using cation exchange chromatography. Column bound peptides and proteins were eluted with buffers systems of various pH values and eluates were subjected to reversed phase chromatography (example 1). To identify fractions blocking HIV-1 infection, peptide fractions were dissolved in PBS and added to HIV permissive indicator cells. Cells were then infected with CXCR4 tropic HIV-1 and infection rates were determined three days post infection (dpi) (example 1). One fraction displayed potent anti HIV activity and was subjected to further rounds of chromatographic purification and HIV inhibition assays aimed to identify the biological active peptide (example 1). After four rounds of purification, mass spectroscopy of the active fraction 31 revealed a single peptide with a molecular weight of 1830 Da (example 2). Sequence analyses resulted in the identification of LVRYTKKVPQVSTPTL (SEQ ID NO: 8) and sequence comparison showed a 100% homology to the highly abundant serum protein "Human Serum Albumin; (ALB)" encompassing amino acid residues 408-423 (ALB408-423) (example 2). Proof of activity was demonstrated as the chemically synthesized peptide (example 3) dose dependently blocks X4 tropic HIV-1 infection (example 4). ALB408-423 specifically blocks X4 tropic HIV-1 variants but has no effect on R5 tropic HIV-1 (example 4 and 5) infection in indicator cells. ALB408-423 also suppressed infection of X4 tropic HIV-2 (example 5). Data obtained from a structure activity relationship study (SAR) aimed to identify residues crucial for antiviral activity are summarized in example 6 and show that the N terminal integrity of ALB408-423 is important for its antiviral activity. In contrast, truncations at the C terminus of up to 6 amino acid residues did not abrogate antiviral activity.

The SAR study also allowed to identify ALB408-423 derivatives such as ALB408-419 or ALB L408I-419 displaying increased antiviral activity compared to wild type ALB408-423 (example 6). None of the ALB derivatives is cytotoxic (example 7). ALB408-423, ALB408-419 and ALB L408I-419 dose dependently blocked infection of a variety of X4 tropic but not R5 tropic HIV-1 variants in indicator cells (example 8) or primary blood mononuclear cells (example 9). All these data indicate a specific interaction of ALB408-423 or its derivatives with the HIV coreceptor CXCR4.

Using fluorescence based techniques it could be demonstrated that ALB408-423 directly binds to and interacts with CXCR4 thereby preventing binding of CXCL12, the natural CXCR4 agonist (examples 10-12). ALB408-423 or its derivatives alone do not induce $Ca^{2+}$ mobilization via CXCR4 or other chemokines receptor such as CCR5 and CXCR1 indicating that ALB408-423 is a CXCR4 antagonists per definition (examples 10-12 and 14). In the presence of ALB408-423, CXCL12 mediated cell migration (example 13) and CXCR4 receptor internalization could be blocked as well providing further evidence that ALB408-423 is a CXCR4 antagonist (example 12). Taken together, ALB408-423, a human serum albumin fragment was identified by screening a HF derived peptide library using an HIV-1 infection inhibition assay. The chemically synthesized peptide and derivatives thereof dose dependently block X4 tropic HIV-1 and HIV-2 infection by a direct interaction with the CXCR4 receptor. ALB408-423 and its derivatives act antagonistically as they do not mediate cellular responses and suppress activity of CXCL12, the natural occurring CXCR4 agonist. These data are evidence that ALB408-423 is the first human CXCR4 antagonist. ALB408-423 and its derivatives might be useful in the treatment of individuals infected with X4 tropic HIV-1, to prevent cancer metastasis and to interfere with chronic inflammatory diseases where CXCR4/CXCL12 signaling is involved and suppresses CXCL12 mediated signaling through CXCR4.

The peptide according to the invention as well as analogues, fragments and derivatives of the peptide, its cDNA, its gene and antibodies that neutralize the activity of ALB408-423 can be employed as medicaments. Its biological activity corresponds to that of virus-inhibiting, cancer cell migration inhibiting and CXCR4 antagonistic substances. ALB408-423 specifically binds CXCR4 thereby preventing infection of CXCR4 tropic HIV-1 variants and binding of the natural CXCR4 agonist CXCL12. The peptide according to the invention can be administered in a way usual for peptides on a parenteral, intravenous, intramuscular, intranasal, localtopic, subcutaneous or buccal route. The amount of peptide to be administered is from 1 μg to 1 g per unit dose per day. The activity of the peptide according to the invention can be inhibited by administering appropriate inhibitors/antagonists.

The diagnostic agent according to the invention contains poly- or monoclonal antibodies against the peptide according to the invention, optionally in a fluorescence-labeled or radioactively labeled form, to be employed in a per se known ELISA or RIA. The diagnostic agent according to the invention contains DNA, RNA and/or PNA, optionally in a modified and/or labeled form, for use in test systems known to the skilled person, such as PCR or fingerprinting. Alternatively, the diagnostic agent according to the invention consists of a mass-spectrometric method (MALDI or ESI-MS) that unequivocally detects the substance qualitatively and quantitatively from its singly of multiply charged ions (parent ions or product ions after MS-MS fragmentation) after a corresponding sample preparation and enrichment (separation of large proteins by precipitation, enrichment of ALB408-423 by chromatography or RP media, solid-phase extraction).

The invention will now be further described by means of the following Examples.

Example 1

Isolation of the Antivirally Effective ALB408-423 from Human Hemofiltrate

Human hemofiltrate is optionally diluted with water and acidified. The pH value is preferably from 1.5 to 3.5, especially from 2.5 to 3.0. Thereafter, the hemofiltrate is passed through a cation exchanger, for example, a support material modified with sulfonic acid groups (Fraktogel SP-650 (M), MERCK, Darmstadt, Germany). The peptides bound to the cation exchanger are eluted with a relatively high concentration of a salt solution. The ionic strength of the eluate is about that of a 0.5 to 1 M ammonium acetate solution.

The collected eluate is subjected to another cation exchange chromatography. This chromatography is preferably a fractional elution with buffers having increasing pH values.

The fractions containing the peptide according to the invention are further purified by preparative reverse-phase chromatography followed by semipreparative reverse-phase chromatography, for example, on C18-modified support materials. The degree of purification is preferably monitored using analytical reverse-phase chromatography, for example, on C18-modified support materials.

1st Step: Hemofiltrate Batch Extraction

From 800 to 1000 liters of hemofiltrate is adjusted to a pH value of 2.7 with HCl and diluted with water to a conductivity of 5.5 mS/cm, and charged onto a strong cation exchanger with a flow rate of 3 l/min.

Chromatographic Conditions:
  Column: Vantage VA 250 (AMICON, Witten, Germany)
  Column material: Fractogel TSK SP 650 (M), 25 cm×20 cm
  Flow rate: 3 l/min
  Detection: 280 nm, pH, conductivity
  Buffer A: Hemofiltrate pH 2.7, conductivity 5.5 mS/cm
  Buffer B: 0.5 M ammonium acetate
  Equipment: Autopilot Chromatographic System (PERSEPTIVE BIOSYSTEMS, Wiesbaden, Germany)

After charging the total of 1,000 liters of liquid over night, rinsing is effected with several column volumes of 5 mM HCl. The elution of the bound peptides is effected as a batch elution with 0.5 M ammonium acetate. A complete elution of the peptides is achieved through a ramping pH value (6.8 to 7.2) and ramping conductivity (56 mS/cm) in about 5 liters of eluate.

2nd step: First Preparative Separation (Batch 01/2003)

The ammonium acetate eluates of the batch extraction are combined in an amount of 10,000 liters of hemofiltrate peptide. After adjusting the pH to 2.7, the peptide extract is charged onto the preparative cation exchanger with the addition of completely desalted water having a conductivity of 5.5 mS/cm.

Chromatographic Conditions:
  Column: Vantage 250 VA
  Column material: Fractogel TSK SP 650 (M), 25 cm×20 cm
  Flow rate: up to 3 l/min during the charging
    0.5 to 1 l/min during elution
  Detection: 280 nm, pH, conductivity
  Sample: Hemofiltrate pH 2.7, conductivity 5.5 mS/cm Equipment: Autopilot Chromatographic System (PerSeptive Biosystems, Wiesbaden, Germany)

After charging the raw extract over 240 min, the column is rinsed with 0.01 M HCl until the conductivity is below 1 mS/cm. Elution is performed in several steps with the buffers stated below.

| Buffer | pH value | Buffer substances | Conductivity (mS/cm) |
|---|---|---|---|
| Washing buffer | 2.0 | 0.01 M HCl | 1 |
| Elution buffer 1 | 3.6 | 0.1 M citric acid monohydrate | 2.9 |
| Elution buffer 2 | 4.5 | 0.1 M acetic acid + 0.1 M sodium acetate | 4.0 |
| Elution buffer 3 | 5.0 | 0.1 M malic acid | 6.2 |
| Elution buffer 4 | 5.6 | 0.1 M succinic acid | 6.1 |
| Elution buffer 5 | 6.6 | 0.1 M $NaH_2PO_4$ | 4.9 |
| Elution buffer 6 | 7.4 | 0.1 M $NaH_2PO_4$ | 6.7 |
| Elution buffer 7 | 9.0 | 0.1 M ammonium carbonate | 6.7 |

Eluates 1-7 are designated as pH pool I-VII. They are separately collected and finally rinsed with completely desalted water. Elution is effected until a new base line is reached, elution volumes of from 10 to 25 liters being reached for the individual pH pools I to VII.

3rd step: Second Preparative Separation:

The individual pH pools are separated by reverse-phase chromatography for fractionating and simultaneous desalting.

Chromatographic Conditions:
Column: FINELINE 100 (Pharmacia, Freiburg, Germany)
Column material: Source RPC, 15 µm
10×12.5 cm (FINELINE 100)
Flow rate: 150 ml/min (FINELINE 100)
Detection: 280 nm, conductivity, pH
Buffer A: 10 mM HCl
Buffer B: 80% acetonitrile in 10 mM HCl
Gradient: 0-60% buffer B in 5 column volumes After charging the individual pH pools, the column is washed with buffer A. During elution, fractions of 200 ml are collected. The fractions are freeze-dried and stored at −20° C. Aliquots of the fractions formed are tested in an HIV inhibition assay. Fractions 6-8 from pH pool II contained the peptide according to the invention.

FIG. 1A-F: Isolation of ALB408-423 from human hemofiltrate. The hemofiltrate fractionated by means pf pH step elution was further fractionated by RP-HPLC, and the fractions obtained were measured in an HIV inhibition test. Control: T20 control.

A. 3rd step of isolation. The RP fractionation of pH pool 2 showed inhibitory activity in fractions 6-8.

B-E. 4th to 7th steps of the isolation. The inhibitory activity was purified until a pure substance was obtained.

F. Mass spectrum (MALDI-MS) and sequence analysis of the purified ALB408-423.

HIV inhibition test were performed by seeding 4000 P4-R5 MAGI cells (P. Charneau et al., J. Mol. Biol. 241: 651, 1994) in 100 µl of DMEM (10% FCS, 100 U/ml penicillin G, and 100 µg/ml streptomycin sulfate). P4-R5 cells are stably transfected with an LTR-lacZ cassette and upon successful infection by HIV-1 will express—galactosidase in a Tat-dependent manner, which can be detected in a chemiluminescence test. On the following day, aliquots of the fractions were added. Therefor the lyophilized fractions were resuspended in 80 µl of DMEM, and 25 µl each thereof was pipetted to P4-R5 cells, incubated at 37° C. for 1 hour and subsequently infected with HIV-1 NL4_3 (1 ng of p24 antigen). Virus stocks were obtained by transient infection of 293T cells with proviral DNA by the calcium phosphate method (CalPhos™ Mammalian Transfection Kit, Clontech). Virus stocks were harvested 48 hours post transfection, filtrated and used for infection. Three days post infection, β-galactosidase activity in infected P4-R5 cells was detected using GalScreen assay (TROPIX) as recommended by the manufacturer. Briefly, supernatant was removed, 40 µl of a 1:1 dilution of PBS/GalScreen+substrate was added, followed by incubation at room temperature for 30 min. Then 30 µl of the lysates were transferred into 96 well lumiplates. Subsequently, the lumines-cence was detected as relative light units per second in a luminometer (Berthold, ORION). From all measurements, the mean β-galactosidase background activity of non-infected control cells was subtracted. % infection values for each infection were calculated relative to no peptide containing controls (100%). The enzyme activities in measurements without ALB408-423 were set at 100%, and all other values were based thereon. The final purification (7th step) was examined under exactly the same conditions in TZM-bl cells (X. Wei et al., Antimicrob. Agents Chemother. 46: 1896, 2002).

Figure 1B:
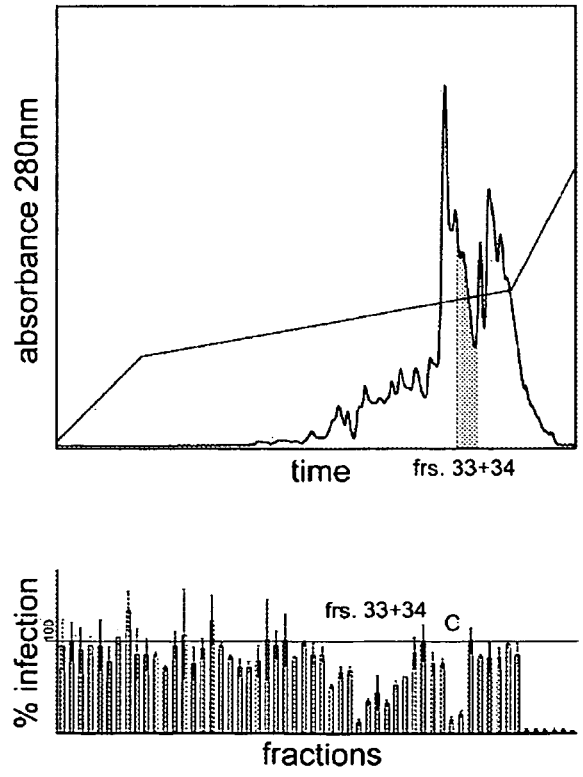

4th step: Semipreparative Reverse-Phase C18 Chromatography:

A total of 200 mg (corresponding to 1087 liters of hemofiltrate equivalent amount) of fractions 6-8 from pH pool II, which were bioactive in the assay (FIG. 1A), was separated through a semipreparative reverse-phase column. Fractions 33+34 contained the substance according to the invention (FIG. 1B).

Chromatographic Conditions:
Column: 4.7 cm×30 cm steel column
Packing material: Bakerbond RP-C18, 15-30 µm, 300 Å
Buffer A: 100% water, 10 mM HCl
Buffer B: 80% acetonitrile, 20% water, 10 mM HCl
Gradient: 0-30% B in 2000 ml
Flow rate: 40 ml/min (pressure: 40 bar)
Detection: 214 nm and 280 nm
Chromatographic
equipment: BioCad 250, PERSEPTIVE BIOSYSTEMS
Fractions: 50 ml each from start of gradient (min 10.75)

5th step: Semipreparative Reverse-Phase C18 Chromatography:

Fractions 33+34 from the previous chromatographic step, which were bioactive in the assay, were separated through a similar semipreparative reverse-phase column using different mobile phases. Subsequent HIV infection assays revealed that fractions 5+6 contained the substance according to the invention (FIG. 1C).

Chromatographic Conditions:
Column: 4.7 cm×30 cm steel column
Packing material: Bakerbond RP-C18, 15-30 µm, 300 Å
Buffer A: 30% methanol, 70% water, 10 mM HCl
Buffer B: 100% methanol, 10 mM HCl
Gradient: 0-15% B in 40 ml
15-60% B in 1900 ml
Flow rate: 40 ml/min (pressure: 30 bar)
Detection: 214 nm and 280 nm
Chromatographic
equipment: BioCad 250, PERSEPTIVE BIOSYSTEMS
Fractions: 50 ml each from start of gradient (min 9.75)

6th step: Analytical Reverse-Phase C4 Chromatography:

Bioactive fractions 5+6 from the previous chromatography were separated through an analytical reverse-phase column. Aliquots were tested in a bioassay (HIV inhibition assay). Fractions 51 to 57 contained the substance according to the invention (FIG. 1D).

Chromatographic Conditions:
Column: 2 cm×25 cm steel column
Packing material: RP-C4, 5 µm, 100 Å, Biotek Silica, Östringen, Germany)
Buffer A: water, 0.1% TFA
Buffer B: 80% acetonitrile, 20% water, 0.1% TFA
Gradient: 0-5% B in 2 min, 5-35% B in 60 min, 35-100% B in 3 min
Flow rate: 7 ml/min
Detection: 214 nm and 280 nm
Chromatographic
equipment: Kontron
Fractions: 1 min each from min 1

7th step: Analytical Reverse-Phase C18 Chromatography:

Bioactive fractions 51-57 from the previous chromatography were separated through an analytical reverse-phase column. Aliquots were tested in a bioassay. Fraction 31 contained the substance according to the invention in a pure form (FIG. 1E).

Chromatographic Conditions:
Column: 1 cm×25 cm steel column
Packing material: RP-C18, 5 µm, 300 Å, Vydac (Hesperia, USA)
Buffer A: water, 0.1% TFA
Buffer B: 80% acetonitrile, 20% water, 0.1% TFA
Gradient: 0-15% B in 5 min, 15-45% B in 60 min, 45-100% B in 1 min
Flow rate: 2 ml/min
Detection: 214 nm and 280 nm
Chromatographic
equipment: Kontron
Fractions: 1 min each from min 1

The pure substance according to the invention was contained in fraction 31 and was then examined in a bioassay in a dose-dependent manner and characterized by peptide chemistry (example 2).

Example 2

Mass Determinations

The mass determinations of the peptide isolated from hemofiltrate (from fraction 31 of the 7th step in Example 1) and on the chemically synthesized peptide (Example 3) were performed on a MALDI mass spectrometer (Voyager DE-Pro). The molecular masses of the peptides were determined to correspond to the following mass figures (MW):
ALB408-423, isolated from human hemofiltrate (FIG. 1F): 1830.9 Da
ALB408-423, chemically synthesized peptide: 1830.6 Da Sequence Determination The purified native peptide was analyzed by means of MS-MS coupling analysis (ESI-TRAP) supplied by the company PROTEOMEFACTORY AG, Dorotheenstr. 94, 10117 Berlin (Germany), by a data base comparison of the established ESI MS-MS masses by means of the Mascot search engine, which resulted in the following sequence with the highest probability:

```
LVRYTKKVPQVSTPTL (SEQ ID NO: 8) (FIG 1F).
```

Data Base Comparison

A further data base comparison with the SwissProt data base shows that the peptide sequence has 100% identity with amino acids 408-423 of the human protein serum albumin (Accession No. NP000468), and the sequence contains the amino acids: LVRYTKKVPQVSTPTL (SEQ ID NO: 8).

Purified Fraction 31 is Active in the HIV-1 Inhibition Bioassay 1.6 mg of fraction 31 from the 7th step in Example 1 was dissolved in 160 µl of DMEM. Subsequently, 10 µl of serial dilutions of fraction 31 containing ALB408-423 were added to 60 µl of TZM-bl cells (60 µl) and infected with 1 ng of p24 antigen HIV-1 NL4_3 in a total volume of 100 µl. Three days later, infection rates were determined in a GalScreen assay (see Example 1). Fraction 31 blocked infection by the X4-tropic HIV-1 NL4_3 in a dose-dependent way. The dose which blocked the infection to half the maximum value ($IC_{50}$) was 21.45 µg/ml (FIG. 2).

Figure 2:
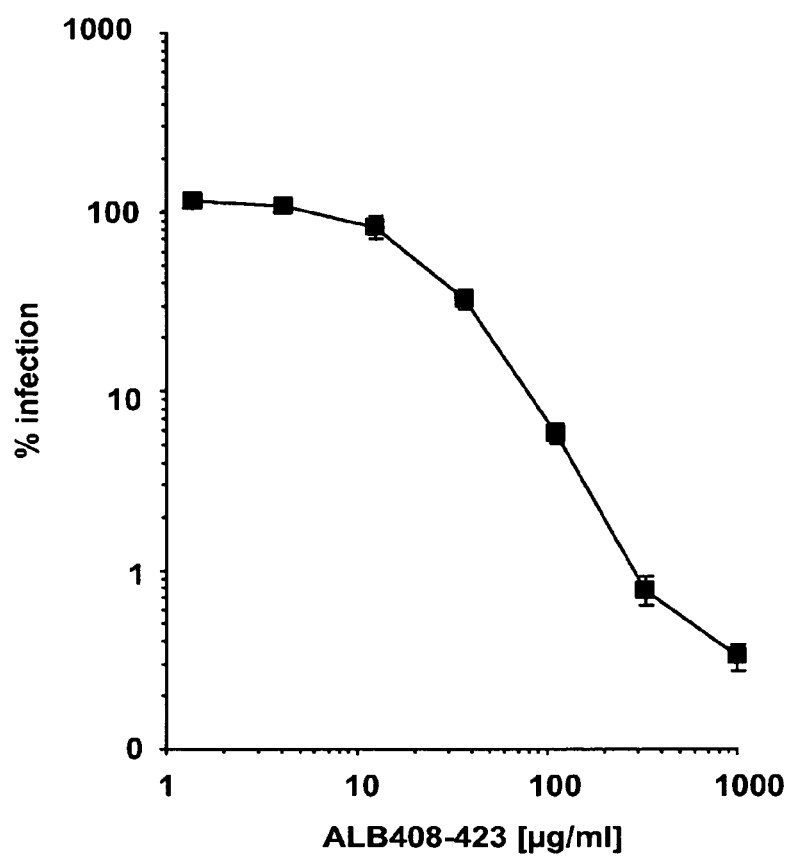
FIG. 2 shows ALB408-423 containing fraction 31 blocks HIV-1 NL4-3 infection.

FIG. 2: ALB408-423 containing fraction 31 blocks HIV-1 NL4-3 infection. TZM-bl cells were incubated with serial dilutions of fraction 31 and were then infected with X4 tropic HIV-1 NL4-3. 3 days later infection rates were determined by GalScreen assay. Shown are mean values±standard deviation from triplicate infections relative to PBS treated controls (100%).

Example 3

Chemical Synthesis of ALB408-423

The chemical synthesis of ALB408-423 was performed by means of conventional solid-phase synthesis on a peptide synthesizer 9050 (APPLIED BIOSYSTEMS) using the known Fmoc chemistry. The peptide obtained was purified by reverse-phase chromatography, and its identity and purity were established by analytical RP-HPLC and by the MALDI-MS mass determination as described under Example 2.

Example 4

Synthetic ALB408-423 Specifically Blocks Infection of X4-Tropic HIV-1 Variants

5000 TZM-bl cells were seeded in 100 µl of DMEM (10% FCS, 100 U/ml of penicillin G and 100 µg/ml of streptomycin sulfate). ALB408-423 was dissolved in PBS (10 mg/ml). One day later, 20 µl serial dilutions of ALB408-423 in PBS were added to cells and cells were subsequently infected with 0.5 ng of p24 antigen HIV-1 in a total volume of 200 µl. HIV-1 molecular clones differing in coreceptor tropism were used and generated as described (Papkalla et al., J. Virol. 76: 8455-9, 2002).

FIG. 3: Chemically synthesized ALB408-423 specifically blocks X4 tropic HIV-1 infection. TZM-bl cells containing indicated dilutions of peptide were infected with HIV-1 variants differing in their coreceptor tropism. 3 days later Gal Screen assay was used to measure infection rates. A) Dose dependent inhibition of X4 tropic HIV-1 variants NL4-3, P51-Sc, P59-S/27 and P34-S or dual tropic 92ht593.1. B) Infection rates in the presence of 500 µg/ml ALB408-423 showing that the peptide specifically blocks X4 but not R5 tropic HIV-1 infection. Data shown are mean values±standard deviation derived from triplicate infections relative to PBS containing cells (100% infection).

After 3 days, infection was detected using GalScreen assay (TROPIX) (example 1). FALB408-423 dose dependently blocked the infection by all analyzed X4-tropic HIV-1 variants (FIG. 3A) (mean $IC_{50}$ of 24.2 µg/ml). The dual tropic (CXCR4 and CCR5 using) variant 92ht593.1 was blocked less efficiently. In contrast, CCR5 tropic HIV-1 variants were not inhibited even in the presence of very high doses of ALB408-423 (500 μg/ml) (FIG. 3B). Due to the specific inhibition of the infection caused by X4-tropic HIV-1 variants, it is to be assumed that ALB408-423 interacts with the chemokine receptor CXCR4.

Both the ALB408-423 purified from hemofiltrate (Example 2) and the chemically synthesized ALB408-423 (Example 4) exhibited a dose-dependent inhibition of HIV-1 replication in target cells providing evidence that ALB408-423 is a natural human HIV-1 inhibitory molecule.

Example 5

Synthetic ALB408-423 Dose Dependently Blocks CXCR4 Tropic Lentiviral Infection

X4 tropic HIV-1 NL4-3 and HIV-2ROD10 or CCR5 tropic HIV-1 NL4-3 92th014, HIV-1-7312 and SIVmac239 were generated by transient transfection of 293T cells and used to infect TZM-bl cells containing indicated concentrations of ALB408-423. Two days later infection rates were determined and calculated as described. (example 4). Results show that ALB408-423 dose dependently blocked X4 tropic HIV-1 and HIV-2 infection ($IC_{50}$~10-20 μM) whereas the peptide had no effect on R5 tropic lentiviral infection demonstrating a specific inhibition of CXCR4 tropic HIV-1 and HIV-2 (FIG. 4).

Figure 4:
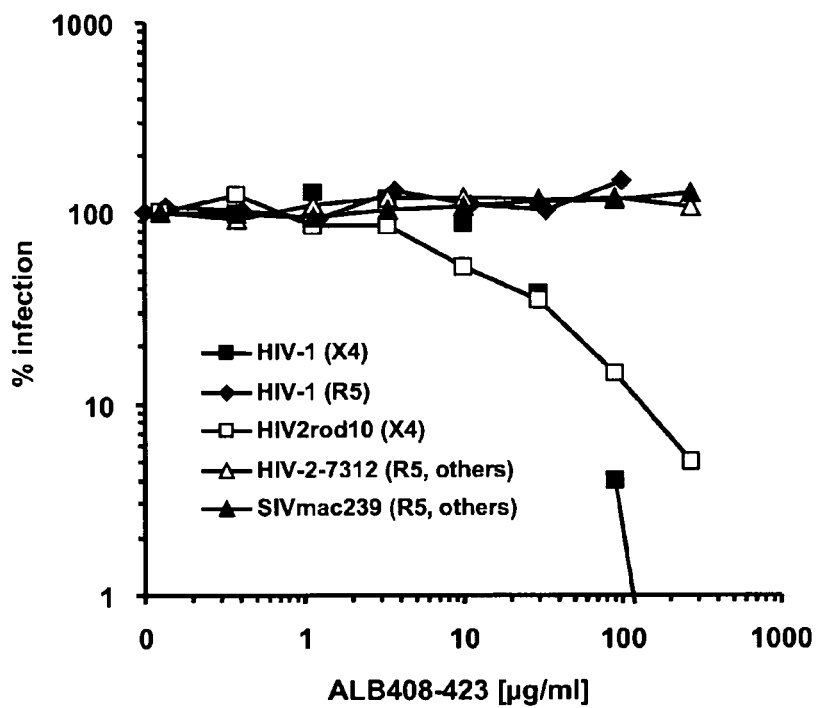
FIG. 4 shows ALB408-423 blocks X4 tropic lentiviral infection.

FIG. 4. ALB408-423 blocks X4 tropic lentiviral infection. Infectivity normalized HIV-1, HIV-2 and SIV stocks were used to infect TZM-bl cells containing ALB408-423. After three days infection rates were determined using the Gal Screen assay. Shown are mean values±standard deviation derived from triplicate measurements. Infection rates of no peptide containing cells=100%.

Table 1. Antiviral activity of various ALB fragments against X4 tropic HIV-1 NL4-3 infection. TZM-bl cells containing serial dilutions of synthetic peptides were infected with HIV-1 NL4-3 and infection rates were determined and calculated as described in example 1 and 2 at two days post infection. $IC_{50}$ values were determined using the GraphPad Prism software package. Abbreviations: Da, molecular weight; $IC_{50}$ μM, half maximal (50%) inhibitory concentration obtained from experiments performed in triplicates; SEM, standard error of the mean; exp, number of experiments performed;

TABLE 1

|  |  | Da | $IC_{50}$ ± SEM | exp | Seq ID No |
|---|---|---|---|---|---|
| ALB415-423 | VPQVSTPTL | 941 | >100 | 3 | 1 |
| ALB414-423 | KVPQVSTPTL | 1068 | >100 | 3 | 2 |
| ALB413-423 | KKVPQVSTPTL | 1196 | >100 | 3 | 3 |
| ALB412-423 | TKKVPQVSTPTL | 1298 | >100 | 3 | 4 |
| ALB411-423 | YTKKVPQVSTPTL | 1461 | >100 | 3 | 5 |
| ALB410-423 | RYTKKVPQVSTPTL | 1618 | >100 | 3 | 6 |
| ALB409-423 | VRYTKKVPQVSTPTL | 1717 | >100 | 3 | 7 |
| ALB408-423 | LVRYTKKVPQVSTPTL | 1832 | 7.6 ± 1.2 | 7 | 8 |
| ALB408-422 | LVRYTKKVPQVSTPT | 1720 | 11.8 ± 3.1 | 4 | 9 |
| ALB408-421 | LVRYTKKVPQVSTP | 1619 | 11.3 ± 3.3 | 4 | 10 |
| ALB408-420 | LVRYTKKVPQVST | 1522 | 11.2 ± 2.9 | 4 | 11 |
| ALB408-419 | LVRYTKKVPQVS | 1422 | 4.4 ± 1.0 | 8 | 12 |
| ALB408-418 | LVRYTKKVPQV | 1334 | 18.3 ± 6.8 | 4 | 13 |
| ALB408-417 | LVRYTKKVPQ | 1232 | 19.9 ± 4.1 | 2 | 14 |
| ALB408-416 |  | n.d. | n.d. |  | 15 |
| ALB408-415 | LVRYTKKV | 1006 | 17.4 ± 6.5 | 2 | 16 |
| ALB408-414 | LVRYTKK | 907 | >50 | 2 | 17 |
| ALB408-413 | LVRYTK | 779 | >50 | 2 | 18 |
| ALB407-414 | LLVRYTKK | 1025 | >100 | 2 | 19 |
| ALB407-419 | LLVRYTKKVPQVS | 1536 | 11.1 ± 1.0 | 2 | 20 |
| ALB408I-419 | IVRYTKKVPQVS | 1421 | 1.55 ± 1.2 | 4 | 21 |
| ALB408F-419 | FVRYTKKVPQVS | 1454 | 93.2 ± 2.1 | 2 | 22 |
| ALB408A-419 | AVRYTKKVPQVS | 1378 | >100 | 2 | 23 |
| ALB408G-419 | GVRYTKKVPQVS | 1366 | >100 | 2 | 24 |

TABLE 1-continued

|  |  | Da | IC$_{50}$ ± SEM | exp | Seq ID No |
|---|---|---|---|---|---|
| ALB408-415 variants |  |  |  |  |  |
| ALB-wt | LVRYTKKV | 1006 | 17.4 ± 6.5 | 2 | 25 |
| ALB-V415A | LVRYTKKA | 978 | 33.0 | 1 | 26 |
| ALB-K414A | LVRYTKAV | 949 | 31.0 | 1 | 27 |
| ALB-K413A | LVRYTAKV | 949 | 56.0 | 1 | 28 |
| ALB-T412A | LVRYAKKV | 976 | 11.2 ± 0.1 | 2 | 29 |
| ALB-Y411A | LVRATKKV | 914 | 91 | 1 | 30 |
| ALB-R410A | LVAYTKKV | 921 | >1000 | 1 | 31 |
| ALB-V409A | LARYTKKV | 978 | 32.9 | 1 | 32 |

Example 6

Structure Activity Relationship (SAR) Study Using ALB408-423 Derivatives

Various ALB408-423 derivatives containing N or C terminal deletions or amino acid substitutions (Table 1) were chemically synthesized and lyophilized peptides were dissolved in PBS. The antiviral activity was analyzed in TZM-bl cells using X4 tropic HIV-1 NL4-3 as described (example 4). N terminal deletions of ALB408-423 (409-423, 410-423, 411-423, 412-423, 413-423, 414-423, 415-423) severely impaired or abrogated antiviral activity indicating that the N terminal Leucine (L408) is crucial for ALB408-423 mediated inhibition of X4 tropic HIV-1 (FIG. 5 and FIG. 6).

Figure 5:
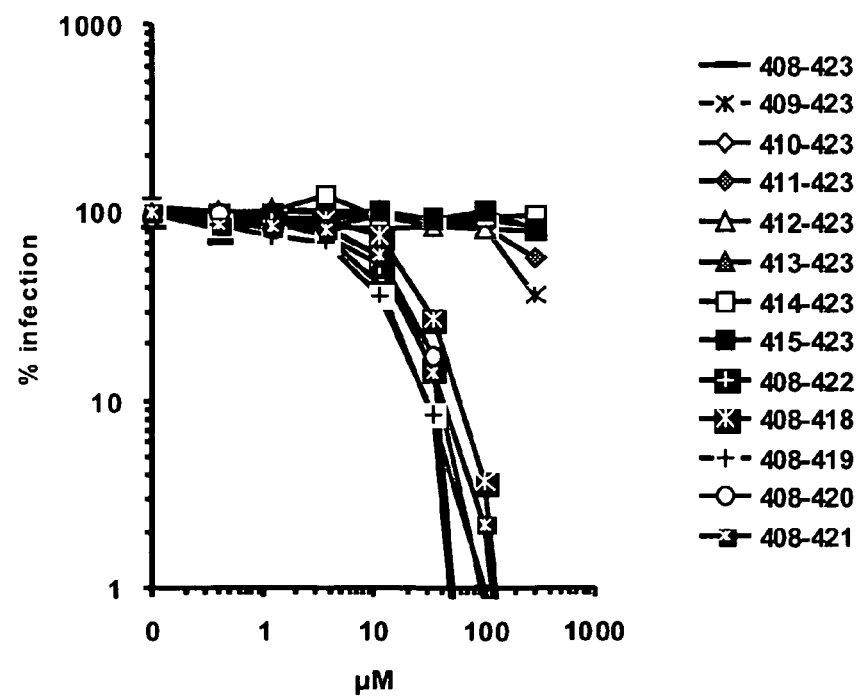
FIG. 5 depicts antiviral activities of ALB derivatives.

FIG. 5. Antiviral activities of ALB derivatives. TZM-bl cells containing serial dilutions of ALB derivatives were infected with X4 tropic HIV-1 NL4-3. After 2 days infection rates were determined by GalScreen assay. Shown are mean values derived from triplicate infections relative to no peptide containing samples (infection rate=100%).

Figure 6:
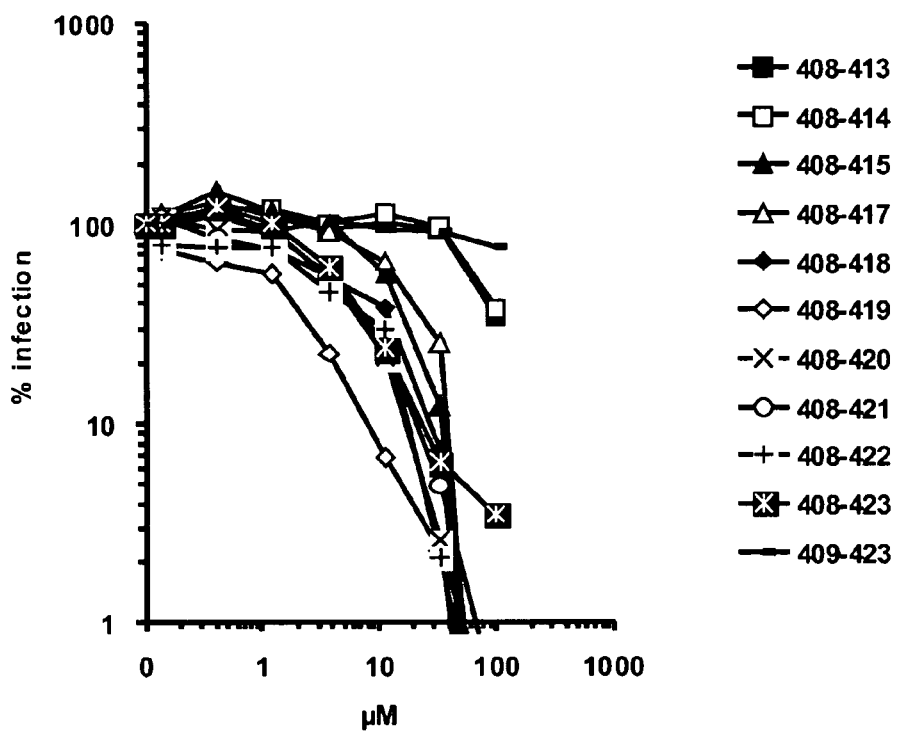
FIG. 6 shows antiviral activities of ALB derivatives.

FIG. 6. Antiviral activities of ALB derivatives. Serial dilutions of ALB derivatives containing TZM-bl cells were infected with X4 tropic HIV-1 NL4-3. After 2 days infection rates were determined by GalScreen assay. Shown are mean values derived from triplicate infections relative to no peptide containing samples (infection rate=100%).

ALB408-423 derivatives containing truncations of up to 8 amino acid residues at the C terminus (408-422, 408-421, 408-420, 408-419, 408-418, 408-417, 408-416, 408-415, 408-414, 408-413) remained active in blocking X4 tropic HIV-1 infection (FIGS. 5 and 6, Table 1). Further deletions at the C terminus (408-414 and 408-413), however, resulted in inactive peptides (IC$_{50}$ values>50 µM) (FIG. 6). Interestingly, the C terminal deletion variant ALB408-419 blocked X4 tropic HIV-1 infection more efficiently than wild type ALB408-423 (4.4±1.0 versus 7.6±1.2; mean IC$_{50}$ values (µM)±sem) (Table 1; FIGS. 5, 6, 7, and 8).

Figure 7:
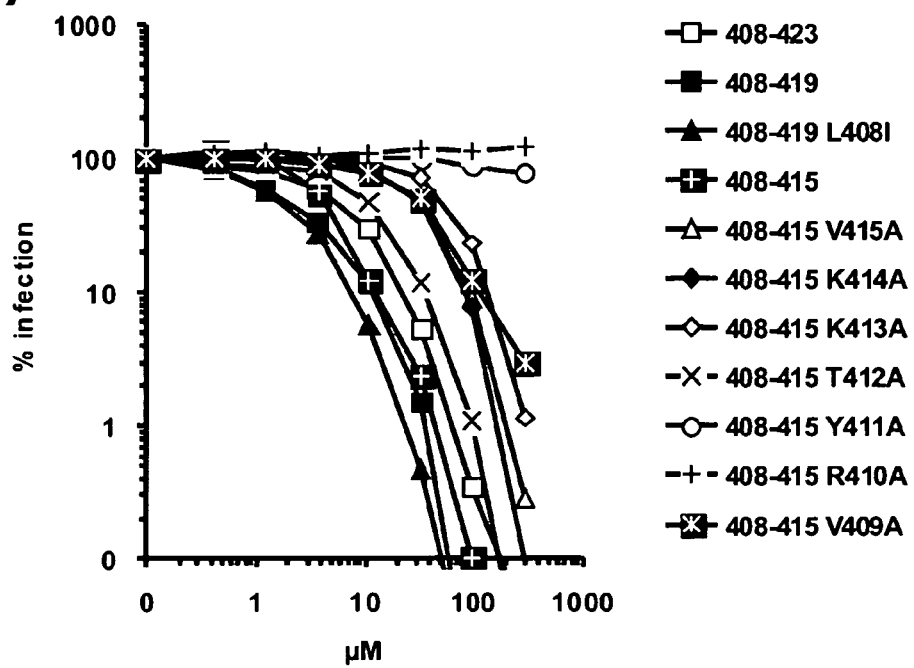
FIG. 7 shows antiviral activities of ALB derivatives.

FIG. 7. Antiviral activities of ALB derivatives. Serial dilutions of ALB derivatives containing TZM-bl cells were infected with X4 tropic HIV-1 NL4-3. After 2 days infection rates were determined by GalScreen assay. Shown are mean values derived from triplicate infections relative to no peptide containing samples (infection rate=100%).

Figure 8:
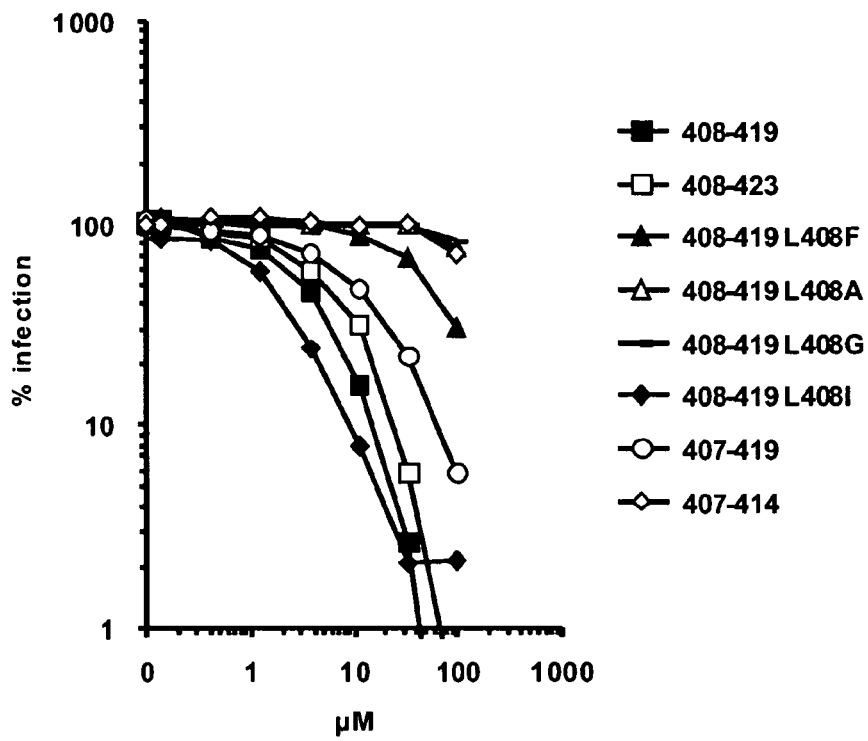
FIG. 8 shows antiviral activities of ALB derivatives.

FIG. 8. Antiviral activities of ALB derivatives. Serial dilutions of ALB derivatives containing TZM-bl cells were infected with X4 tropic HIV-1 NL4-3. After 2 days infection rates were determined by GalScreen assay. Shown are mean values derived from triplicate infections relative to no peptide containing samples (infection rate=100%).

As the only 8 amino acid residues encompassing ALB408-415 derivative displayed potent antiviral activity (17.4±6.5), an Alanine scan was performed by synthesizing and testing ALB408-415 derivatives containing specific amino acid substitutions (Table 1). Data shown in FIG. 7 and Table 1 demonstrate that most substitutions impaired antiviral activity of ALB408-415. In particular Arginine 410 (ALB-R410A, IC$_{50}$>1000 µM versus ALB408-415; 17.4±6.5 versus) plays an important role in HIV-1 inhibition (FIG. 7, Table 1). Substitution of Threonine 412 to Alanine (ALB-T412A) resulted in a peptide with moderately increased antiviral activity (11.2±0.1) (FIG. 7 and Table 1).

To further elucidate the role of the N terminal Leucine (L408) for antiviral activity of ALB408-419, this residue was replaced by Phenylalanine (F), Alanine (A), Glycine (G) or Isoleucine (I). HIV-1 inhibitions assays revealed that most substitutions at the N terminus resulted in inactive peptides (ALB408F-419, ALB408A-419 and ALB408G-419) (FIG. 8). However, the homologous exchange to Isoleucine (ALB L408I-419) resulted in a peptide with moderately increased antiviral activity (1.55±1.2)(FIG. 8). An additional Leucine at the N terminus of ALB408-419 (407-419) reduced its antiviral activity (FIG. 8).

Taken together, SAR analysis allowed to identify truncated ALB derivatives with increased antiviral activity and showed that in contrast to the C terminus, the N terminal part is crucial for ALB408-423 mediated inhibition of X4 tropic HIV-1 infection.

Example 7

None of the ALB Derivatives is Cytotoxic

To assess possible cytotoxic effects of ALB variants, 5×103 TZM-bl cells were incubated with increasing concentrations of those peptides exerting most potent antiviral activity (Table. 1 and FIG. 9) for 3 days. Cell viability was determined using the CellTiter-Glo Luminescent Cell Viability Assay (PROMEGA, #G7571) as recommended by the manufacturer. This luminescence based assay measures the number of viable cells based on the amount of intracellular ATP. Data were recorded using a luminometer 10 minutes after adding reagent. Luminescence activities derived from cells incubated with PBS only were set to 100%. Results shown in FIG.

9 clearly show that none of the tested ALB derivatives displayed cytotoxic effects at concentrations up to 300 µM.

Figure 9:
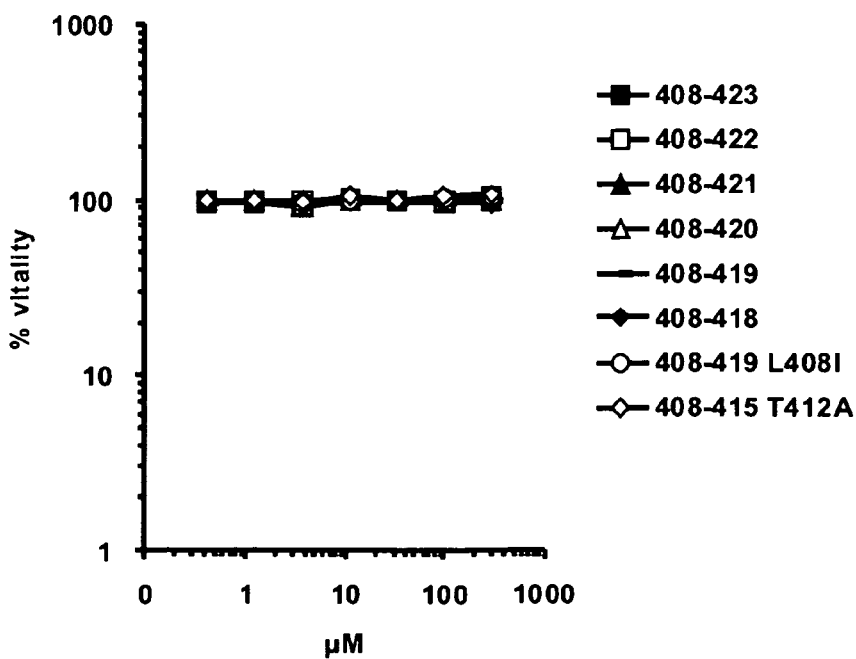
FIG. 9 shows cytotoxicity assay of ALB derivatives.

FIG. 9. Cytotoxicity assay of ALB derivatives. Serial dilutions of ALB derivatives were added to TZM-bl cells. After 2 days cellular ATP levels were measured using the CellTiter-Glo Luminescent Cell Viability Assay. Values were derived from triplicate measurements. % vitality rates were calculated relative to ATP levels in PBS (no peptide) containing cells (100%).

Example 8

Antiviral Activity of ALB408-423 and Most Potent Derivatives

Figure 10:
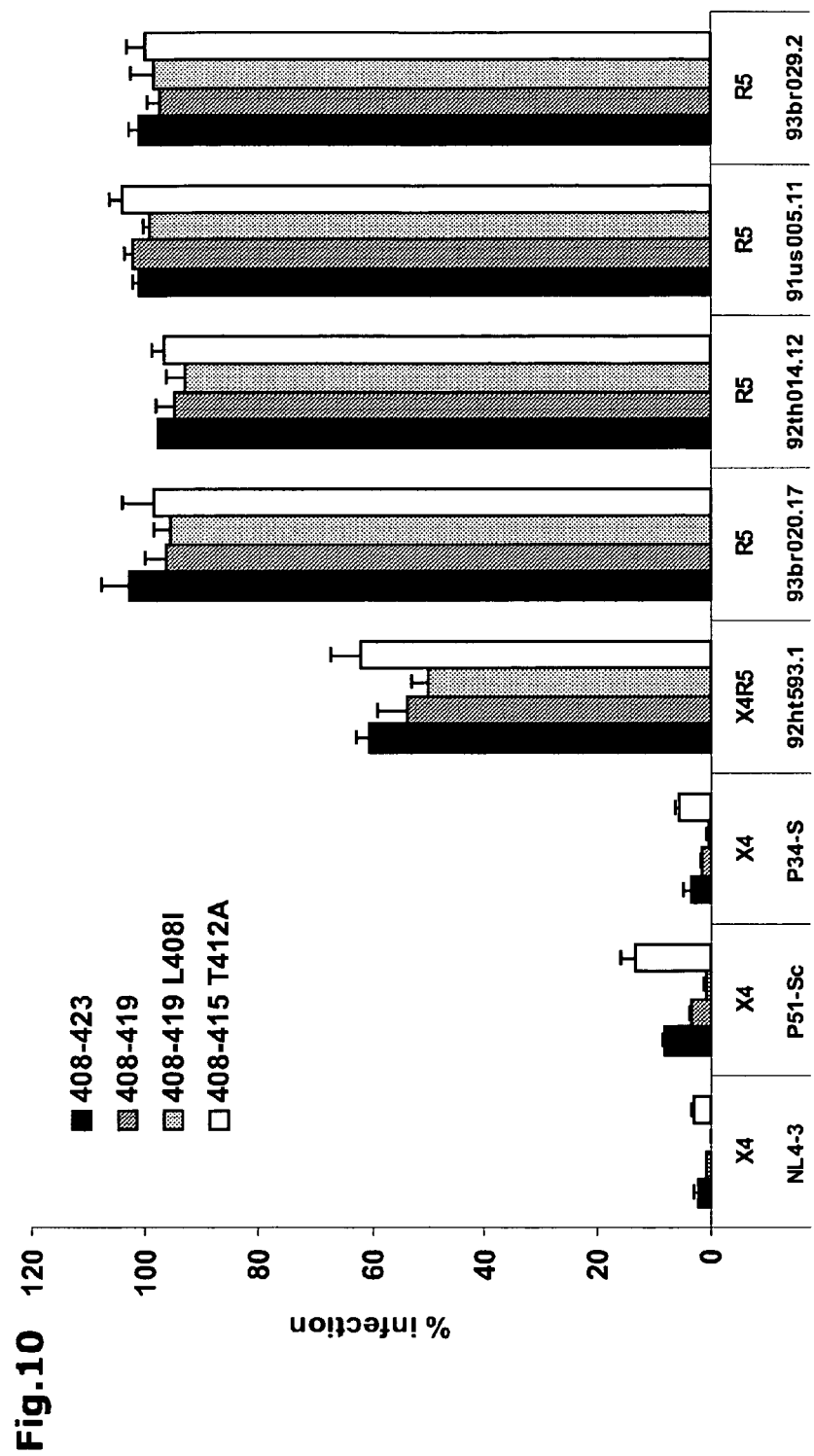
FIG. 10 shows ALB408-423 and truncated ALB derivatives specifically block X4 tropic HIV-1 infection.

To investigate the effect of most active ALB peptides on various HIV-1 clones, viruses differing in coreceptor use were generated by transfection of 293T cells with proviral plasmids (Papkalla et al., J. Virol. 76: 8455-9, 2002). Virus stocks were first titrated on TZM-bl cells. Then TZM-bl cells containing 100 µM of peptides were infected with infectivity normalized amounts of X4, dualtropic (X4/R5) or R5 tropic HIV-1. Infection rates were determined as described (example 4) showing that wild type ALB408-423, the C terminal truncated ALB408-419 and ALB L408I-419 variants as well as ALB-T412A blocked infection of all analyzed X4 tropic HIV-1 clones (NL4-3, P51-Sc, P34-s) almost completely (FIG. 10). The peptides had no effect on R5 tropic HIV-1 infection and inhibited infection of TZM-bl cells by dualtropic HIV-1 clone 92ht593.1 only moderately. These data demonstrate that ALB variants with increased antiviral activity (compared to ALB408-423) (Table 1) are also broad spectrum inhibitors of X4 tropic HIV-1 variants.

FIG. 10. ALB408-423 and truncated ALB derivatives specifically block X4 tropic HIV-1 infection. TZM-bl cells either containing PBS or 100 µM of indicated peptides were infected with normalized infectivities of X4, dualtropic or R5 tropic HIV-1 clones. Infection rates were measured 2 days post infection using the GalScreen assay. Shown are mean values (% of PBS treated control)±standard deviations derived from triplicate measurements.

Example 9

Figure 11:
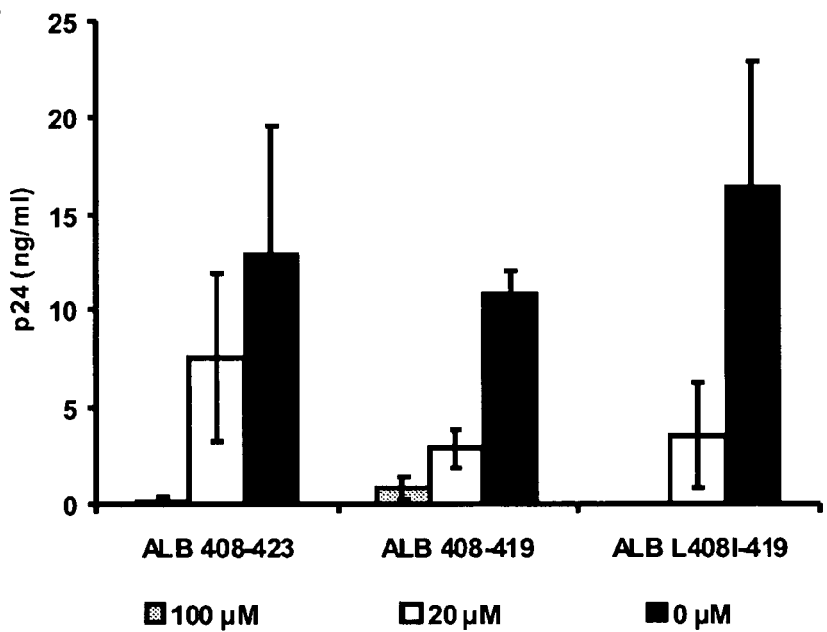
FIG. 11 shows ALB408-423 and derivatives inhibit X4 tropic HIV-1 infection of peripheral blood mononuclear cells (PBMC).

ALB408-423, ALB408-419 and ALB L408I-419 Block X4 Tropic HIV-1 Infection and Replication in PBMC To analyze the effect of ALB408-423 and derivatives thereof in relevant primary cells, peripheral blood mononuclear cells were isolated from Buffy coat derived from the DRK-Blutspendedienst Baden-Württemberg-Hessen using Ficoll density centrifugation. $1 \times 10^6$ PBMC per ml were stimulated with 1 µg/ml phytohemagglutinine (PHA, Oxoid, #3085280) and 10 ng/ml Interleukin 2 (IL-2, Strathmann, #9511192) for three days. Thereafter cells were pelleted and resuspended in IL-2 containing medium. $1.5 \times 10^5$ PBMC (250 µl) were seeded in 96 well dishes, peptides were added and cells were infected with 50 µg/ml p24 antigen of X4 tropic HIV-1 NL4-3. Supernatants containing progeny virus were taken at day 1, 3 and 6 post infection. Virus production was measured by p24 antigen ELISA (SAIC-Frederick, Inc [AIDS & Cancer virus program]). No p24 antigen could be detected in supernatants derived at day 6 from cells containing 100 µM ALB408-423 and ALB L408I-419 and only marginal p24 levels in supernatants containing 100 µM ALB408-419 (FIG. 11). In the presence of 20 µM peptides virus replication was severely impaired. These data demonstrate that ALB408-423 and its two derivatives tested block infection and replication of X4 tropic HIV-1 in natural HIV target cells.

FIG. 11. ALB408-423 and derivatives inhibit X4 tropic HIV-1 infection of peripheral blood mononuclear cells (PBMC). Cells were incubated with indicated concentrations of ALB408-423 or truncated variants and infected with X4 tropic HIV-1. Supernatants obtained after 6 days were analyzed by p24 ELISA. Shown are mean p24 antigen values (ng/ml) derived from triplicate infections±standard deviation.

Example 10

ALB 408-423 Peptide Inhibits Binding of CXCL12 to CXCR4

In order to test the ability of ALB 408-423 to inhibit binding of the chemokine CXCL12 to its receptor, CXCR4, a fluorescent binding assay on whole living cells was performed as previously described (Valenzuela-Fernandez, et al.; 2001, JBC 276:26550-26558). The CXCR4 receptor is stably transfected in Human Embryonic Kidney (HEK) cells as a fusion protein with the EGFP fluorescent protein fused to the extracellular amino-terminal part of the receptor (EGFP-CXCR4). The human chemokines CXCL12 and CXCL12-TexasRed were synthesized as described (Amara et al., 1999, JBC 274:23916-23925; Valenzuela-Fernandez, et al., 2001, JBC 276:26550-26558). Real-time fluorescence monitoring of ligand-receptor interactions was performed as followed: HEK293 cells expressing the fusion receptor, EGFP-hCXCR4, were harvested in phosphate-buffered saline supplemented with 5 mM EDTA, pH 7.4, centrifuged and resuspended in HEPES-bovine serum albumin buffer (10 mM HEPES, 137.5 mM NaCl, 1.25 mM $MgCl_2$, 1.25 mM $CaCl_2$, 6 mM KCl, 10 mM glucose, 0.4 mM $NaH_2PO_4$, 1% bovine serum albumin (w/v), pH 7.4) supplemented with protease inhibitors (40 µg/mL bestatin and bacitracin, 20 µg/mL phosphoramidon, 50 µg/mL chymostatin, and 1 µg/mL leupeptin). Experiments were performed on cells suspended in HEPES-BSA buffer (typically at $10^6$ cells/mL). Time-based recordings of the fluorescence emitted at 510 nm (excitation at 470 nm) were performed at 21° C. using a spectrofluorimeter (fluorolog 2, Spex) and sampled every 0.3 s. Fluorescence binding measurements were initiated by adding at 30 seconds 100 nM of CXCL12-TR to 1 mL cell suspension. For competition experiments, EGFP-CXCR4-expressing cells were pre-incubated for 10 min in the absence or presence of various concentrations of the competitor. Then, CXCL12-TR (100 nM) was added and fluorescence was recorded until equilibrium was reached (300 sec). Data were analyzed using Kaleidagraph 3.08 software (Synergy Software, Reading, Pa., USA). Association with fluorescent CXCL12 is detected as a decrease of EGFP fluorescence emission that results from energy transfer to the Texas-red (TR) group of CXCL12.

CXCL12 binding saturation is reached at concentrations beyond 300 nM and the dissociation constant of fluorescent CXCL12 for the CXCR4 receptor equals 55±15 nM (Valenzuela-Fernandez et al., (2001), JBC 276, 26550-26558), Hachet-Haas et al; (2008), JBC]. Unlabeled molecules competing with fluorescent CXCL12 prevent the decrease of EGFP emission as a function of receptor sites occupancy. The detected variation of fluorescence intensity can be quantified (Palanche et al., (2001), JBC 276:34853-34861; Vollmer et al., 1999, JBC 274:37915-37922; Ilien et al., 2003, Neurochem 85:768-778) to derive binding constants of competitor.

Figure 12:
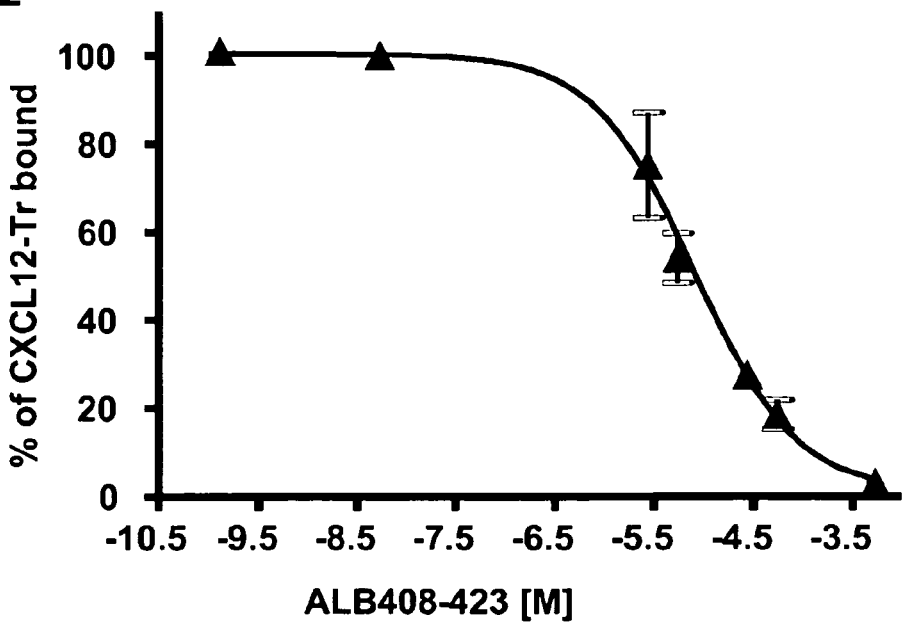
FIG. 12 shows ALB408-423 inhibits binding of CXCL12 to CXCR4.

Our analysis demonstrates that ALB408-423 dose dependently prevents interaction of CXCL12-Tr with its receptor CXCR4 (FIG. 12). ALB408-423 exhibits a dissociation constant (EC50) equal to 8±3 µM, corresponding to a KI value equal to 3±1 µM. The dissociation constant EC50 value is similar to the $IC_{50}$ values obtained in HIV-1 inhibition assays.

FIG. 12. ALB408-423 inhibits binding of CXCL12 to CXCR4. Real-time fluorescence monitoring of ligand-receptor interactions were performed using 293 cells expressing EGFP-hCXCR4. Cells were pre-incubated for 10 min in the absence or presence of various concentrations of ALE3408-423. Then, CXCL12-TR (100 nM) was added and fluorescence was recorded until equilibrium was reached (300 sec). Data were analyzed using Kaleidagraph 3.08 software (Synergy Software, Reading, Pa., USA). Shown are mean values±standard deviation obtained from triplicate measurements relative to fluorescence intensities of CXCL12-Tr treated cells only (100%).

Example 11

Peptide ALB408-423 does not Induce $Ca^{2+}$ Mobilization Via CXCR4, CCR5 and CXCR4 and Inhibits CXCL12-Evoked Calcium Cellular Responses The capacity of ALB408-423 to regulate CXCR4, CCR5 or CXCR1-mediated cellular responses was investigated on calcium indicator-loaded HEK293 cells. Intracellular $Ca^{2+}$ release measurement was carried out as described (Palanche et al., 2001, JBC 276:34853-34861; Vollmer et al., 1999, JBC 274:37915-37922) using indo-1 acetoxymethyl ester as the calcium probe. Cellular responses were recorded at 37° C. in stirred 1 mL cuvette with excitation set at 355 nm and emission set at 405 nm and 475 nm using a spectrofluorimeter. The human chemokines CCL5 and CXCL8 were purchased from Becton Dickinson Biosciences (San Jose, Calif.). $Ca^{2+}$ mobilization assays using CXCR4, CCR5 or CXCR1 expressing cells demonstrate that respective chemokine agonists CXCL12 (CXCR4), CCL5 (CCR5) and CXCL8 (CXCR1) induce $Ca^{2+}$ mobilization (FIG. 13) whereas ALB408-423 by itself does not induce any calcium response and hence does not exhibit CXCR4, CCR5 and CXCR1 agonistic properties (FIG. 13).

Figure 13:
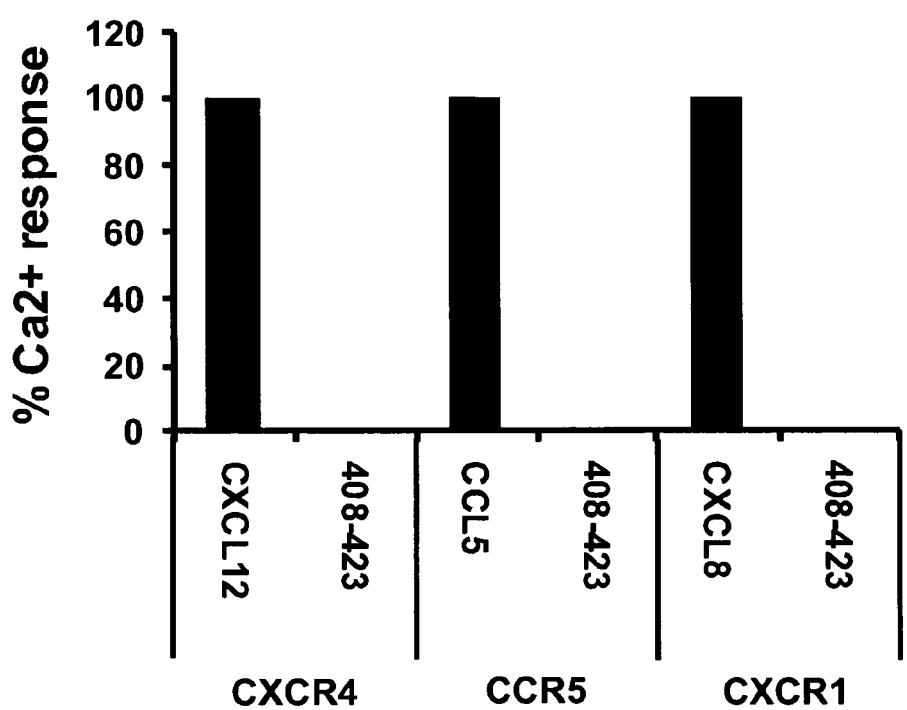
FIG. 13 shows ALB408-423 is not a CXCR4, CCR5 or CXCR1 agonist.

FIG. 13. ALB408-423 is not a CXCR4, CCR5 or CXCR1 agonist. HEK293 cells expressing indicated chemokine receptors were either treated with respective chemokines [10 nM CXCL12 (CXCR4); 20 nM CCL5 (CCR5) or 50 nM CXCL8 (CXCR1)] or 50 µM ALB408-423. Intracellular $Ca^{2+}$ responses were measured using a spectrofluorimeter. Fluorescence intensities obtained after treatment with ALB408-423 are shown relative to those measured for the respective chemokine (100%).

Figure 14A:
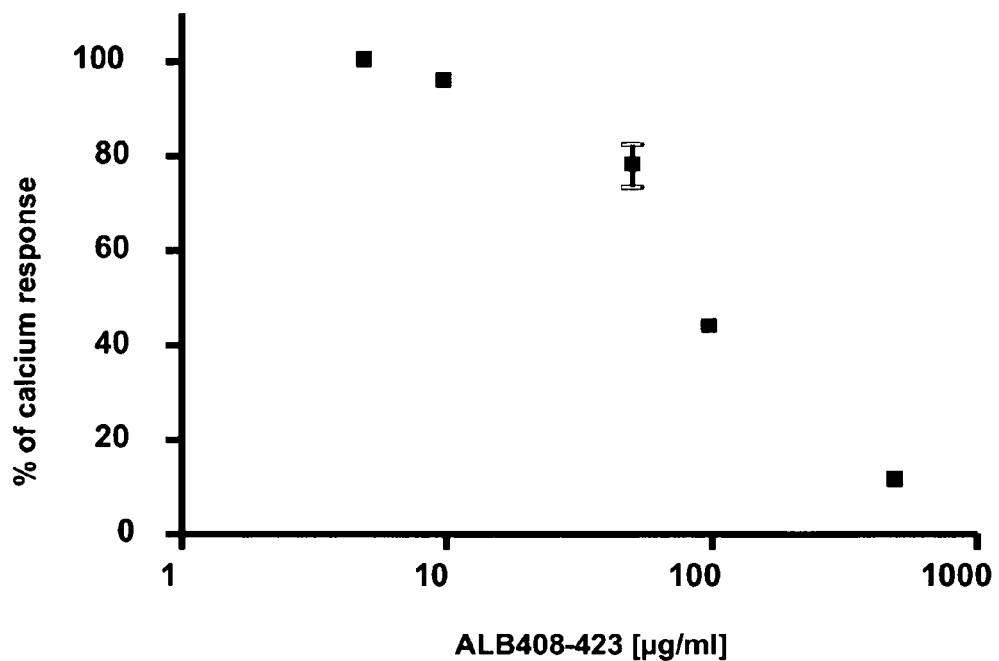
FIG. 14 shows ALB408-423 specifically inhibits CXCL12-evoked $Ca^{2+}$ mobilization in CXCR4 expressing cells.

FIG. 14. ALB408-423 specifically inhibits CXCL12-evoked $Ca^{2+}$ mobilization in CXCR4 expressing cells. A) Dose dependent inhibition of CXCL12 mediated intracellular $Ca^{2+}$ release by ALB408-423. B) ALB408-423 has no effect on CCL5-evoked calcium responses in HEK CCR5 cells or CXCL8-evoked responses in HEK EGFP-CXCR1 cells. Black bars: respective chemokine only; grey bars: respective chemokine and 50 µM ALB408-423. Values shown are mean calcium peak responses from duplicate experiments relative to chemokine only treated cells (100%).

Figure 14B:
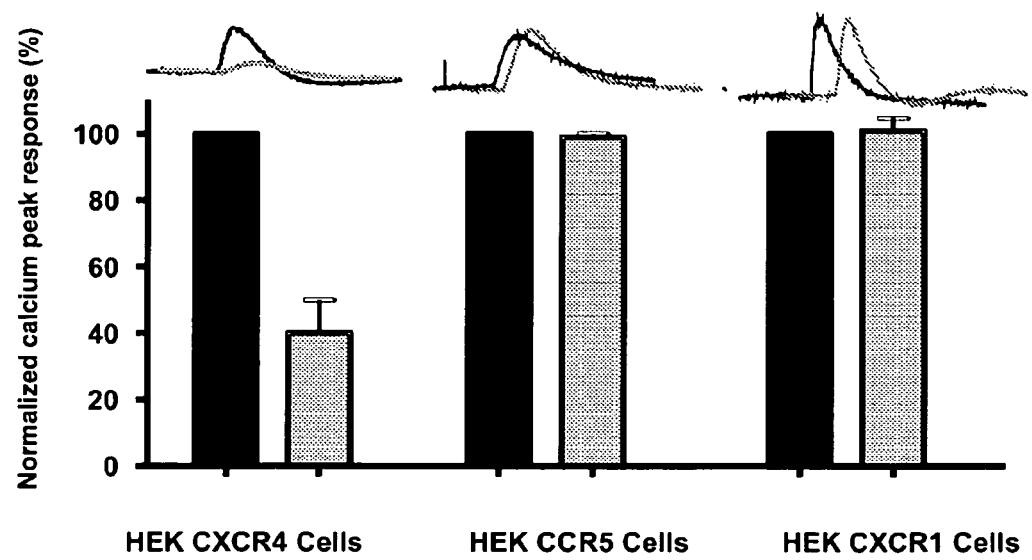

To figure out whether ALB408-423 has CXCR4 antagonistic properties we analyzed the effect of ALB408-423 on binding of the agonist CXCL12 to the CXCR4 receptor. Therefore, CXCR4 expressing cells were incubated with various concentrations of ALB408-423 and then treated with CXCL12. $Ca^{2+}$ responses were recorded. Data shown in FIG. 14A demonstrate that ALB408-423 inhibits CXCL12-evoked calcium responses in a dose-dependent manner and with an apparent inhibitory constant of 85 µg/ml. In order to gain insight into compound selectivity, we next characterized the effect of the peptide on calcium responses of various chemokine/receptor pairs. Consistent with data from FIG. 14A, 50 µM of the peptide inhibit 70% of CXCL12-evoked calcium responses in HEK EGFP-CXCR4 cells (FIG. 14B). In contrast, it has no effect on CCL5-evoked calcium responses in HEK CCR5 cells or on CXCL8-evoked responses in HEK EGFP-CXCR1 cells (FIG. 14B). These results support the idea that the peptide shows selectivity for the CXCR4 receptor and is a CXCR4 antagonist.

Example 12

ALB408-423 Inhibits CXCL12-Evoked CXCR4 Internalization

Upon stimulation with the appropriate chemokine, numerous G-protein-coupled receptors get internalized by clathrin-coated pits. As an antagonist of CXCR4 responses, ALB 408-423 may also alter chemokine induced CXCR4 receptor internalization. To analyze the antagonistic properties of ALB408-423 on CXCL12 mediated CXCR4 internalization, EGFP-CXCR4 receptor expressing cells were split and grown for 2 days in 24-well plates on 12-mm glass coverslips coated with rat type I collagen. The cells were then incubated for periods ranging from 0 to 30 min in HEPES-BSA buffer supplemented with protease inhibitors containing either 100 nM CXCL12 or 50 µM of ALB408-423 or 100 nM CXCL12 plus 50 µM of ALB408-423 at 37° C. Internalization was stopped by placing cells on ice and washing them immediately with ice-cold HEPES-BSA buffer. The cells were then fixed in 4% paraformaldehyde in PBS for 15 min at 4° C. and then incubated for 15 min in NH4Cl 50 mM. Coverslips were mounted onto microscope slides using an anti-fading agent, Möviol (CALBIOCHEM), maintained at room-temperature for 24 hours and then stored at −20° C. Cells were then analyzed with an inverted microscope (LEICA) and a laser scanning confocal imaging system (LEICA AOBS SP2 MP) using a HCX PL APO 1bd.BL 63X 1.40 OIL UV objective (n° 506192). Electronic zoom was set to 3, the pinhole was 1 Airy, and the resulting pixel size was 0.154 µm. EGFP was excited with the 488 nm laser-line of the Argon laser and detected and amplified by one photomultiplier tube (PMT) in the so-called mCFP Channel from 495 to 550 nm (PMT1 610 High Voltage -HV-, offset 0). To obtain a good signal to noise ratio, the images were averaged from 4 consecutive acquisi-tions.

FIG. 15. ALB408-423 blocks CXCL12 mediated CXCR4 internalization. Receptor endocytosis was monitored on HEK cells expressing EGFP-CXCR4 and analyzed by confocal microscopy immediately (0 min, upper panel) after addition of CXCL12, ALB408-423 or both compounds, or 30 min later (lower panel). After 30 min CXCL12 treated cells internalized CXCR4. In the presence of ALB408-423, CXCL12 mediated receptor internalization is abrogated.

Confocal images show that 30 min treatment at 37° C. with 100 nM CXCL12 resulted in the internalization of EGFP-CXCR4 to the periphery of the cell and in vesicular structures (FIG. 15). As expected, ALB408-423 alone did not induce internalization of the receptor, but blocked CXCL12 mediated CXCR4 internalization (FIG. 15) as the majority of fluorescence remained at the cell surface. This result provides further evidence that ALB408-423 acts antagonistically on the CXCR4 receptor.

Example 13

ALB408-423 Blocks CXCL-12 Mediated Migration of Jurkat T Cells

CXCL12-CXCR4 signaling plays a crucial role in several diseases such as HIV/AIDS, cancer, leukemia and arthritis. CXCL12 expressing organs, tissues or cells can attract CXCR4 expressing tumor cells and allow metastasis. To investigate whether ALB408-423 is able to inhibit CXCL12 mediated tumor cell migration, migration assays were performed using Jurkat T cells expressing CXCR4 as model system (Princen et al., 2004, J.Virol. 78: 12996-13006). Jurkat T cells were suspended at 0.4×106 (200 µl) in medium containing 10% FBS, then the cell suspension (200 µl) was added to the upper compartment of 5 µm pore filter devices (Transwell, 24-well cell culture, Costar). Then, 600?l culture medium with or without CXCL12 (100 ng/ml) was added to the lower compartment allowing attraction of cells from the upper compartment. To study inhibitory effects on CXCL12-induced Jurkat T cell migration, CXCL12 in the lower compartment was mixed with various concentrations of ALB 408-423. The cell culture plates were incubated for 2 h in a cell culture incubator at 37° C. After incubation, plates were removed and 100 µl of cells that migrated to the lower compartment were either counted directly using a counting chamber or analyzed using a proliferation assay (CellTiter-Glo® Reagent, PROMEGA) as recommended by the manufacturer. The proliferation assay measures intracellular ATP levels that are directly proportional to cell numbers (data not shown). Data shown in FIG. 16 demonstrate that ALB408-423 dose dependently inhibits CXCL12 mediated Jurkat T cell migration. At high concen-trations (360 µg/ml) ALB408-423 blocked CXCL12 induced cell migration almost completely, comparable to rates observed in the absence of any peptide (no CXCL12, no ALB408-423). These data show that the CXCR4 antagonist ALB408-423 can inhibit attraction of tumour cells mediated by CXCL12.

Figure 16:
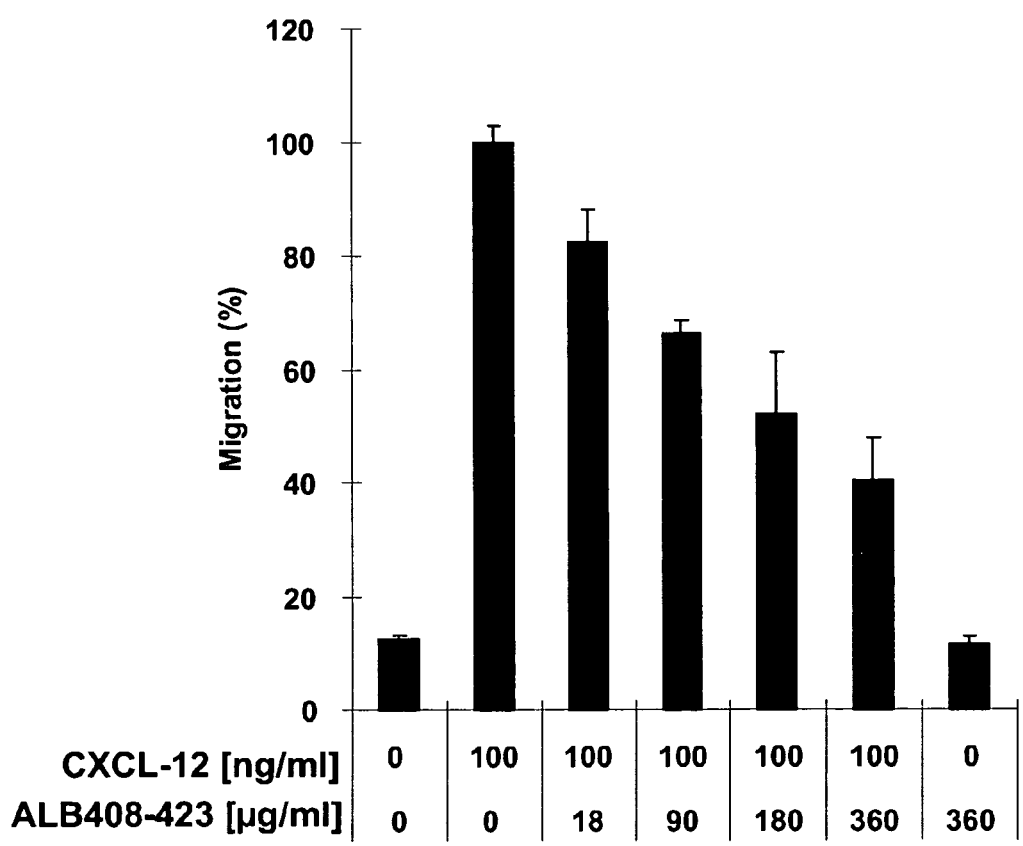
FIG. 16 shows ALB408-423 dose dependently blocks CXCL-12 mediated migration of Jurkat T cells.

FIG. 16. ALB408-423 dose dependently blocks CXCL-12 mediated migration of Jurkat T cells. Jurkat T cells were added to the upper compartment of transwell devices with 5 µm pore filters. Then PBS, CXCR4 agonist CXCL12 (100 nM) or serial dilutions of ALB408-423 were added to the lower com-partment of the cell culture plate. After 2 hrs incubation at 37° C., the number of migrated cells in the lower compartment was detected by measuring intracellular ATP levels using CellTiter-Glo® Luminescent Cell Viability Assay kit (PROMEGA). All values represent mean numbers of migrated cells relative to CXCL12 only treated cells (100% migration) from a triplicate experiment±standard deviation.

Example 14

ALB408-423 Binding to CXCR4 Depends on the N-Terminal Amino-Acid Integrity

Figure 17A:
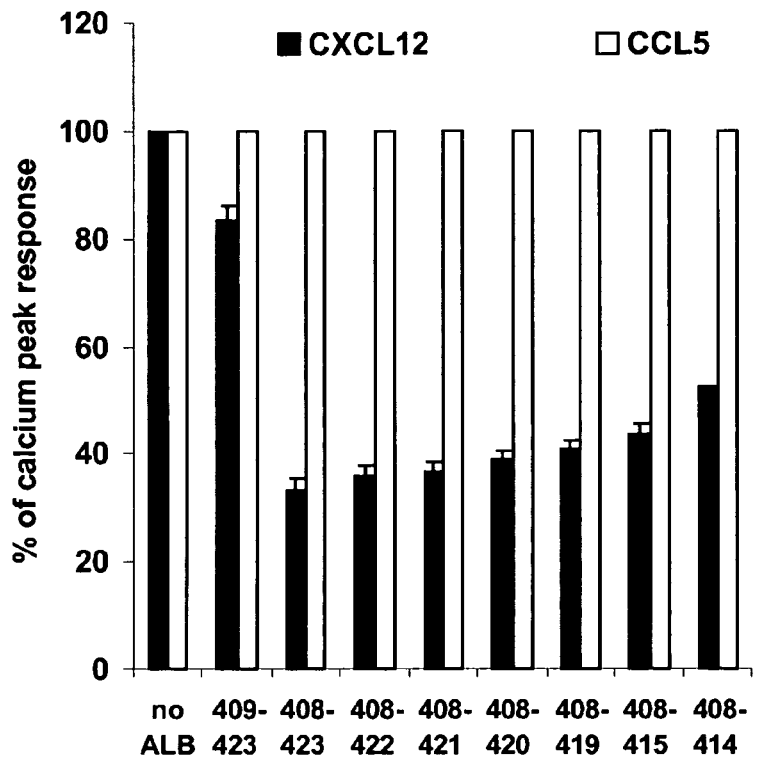
FIG. 17 shows CXCR4 antagonistic activities of ALB derivatives.
Figure 17B:
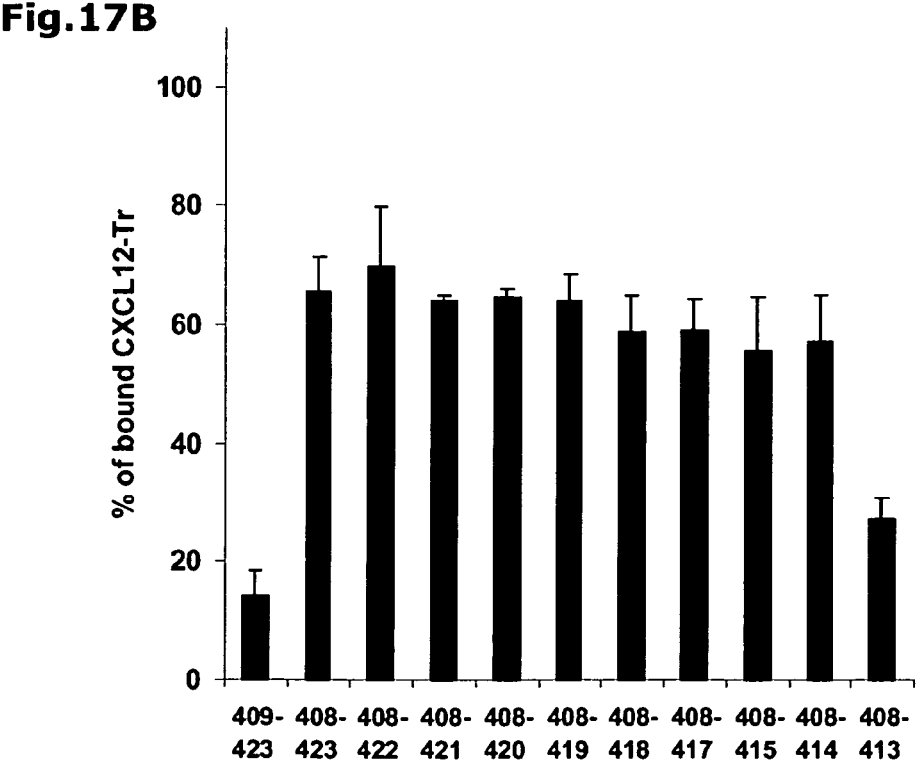

To identify regions in ALB408-423 mediating binding to CXCR4 and hence blocking X4 tropic HIV-1 infection and CXCL12 binding, we analyzed the effect of several ALB408-423 derivatives (see Table 1) on CXCL12 induced $Ca^{2+}$ mobilization and CXCL12-Tr binding. For experimental detail see examples x and y. As shown in FIGS. 17 A and B, ALB409-423 lacking the N terminal Leucine did not inhibit CXCL12 mediated $Ca^{2+}$ responses or binding of CXCL12-Tr to the CXCR4 receptor. Interestingly, ALB409-423 is also inactive in the HIV-1 inhibition assay indicating that the inability of ALB409-423 to bind CXCR4 also accounts for the loss of antiviral activity. In contrast, all C terminal truncated ALB derivatives were still able to interact with the CXCR4 receptor (FIG. 17A) and blocked CXCL12 mediated $Ca^{2+}$ response (FIG. 17B) and exhibit a dissociation constant closed to the wild type peptide (30 µM), except for the smallest, 408-413, which has a lower affinity for the receptor (>200 µM) and is also largely ineffective in blocking X4 tropic HIV-1 infection (FIG. 6 and table 1). Taken together these data show that several C terminal truncated ALB derivatives are CXCR4 antagonists that are able to bind CXCR4 thereby preventing CXCL12 binding and signaling or X4 tropic HIV-1 infection.

FIG. 17. CXCR4 antagonistic activities of ALB derivatives. A) ALB fragments inhibit CXCL12 but not CCL5 evoked $Ca^{2+}$ mobilization. CXCR4 or CCR5 expressing HEK293 cells were treated with CXCR4 agonist CXCL12 (10 nM) or CCR5 agonist CCL5 (20 nM), respectively, in the absence (no ALB) or presence of indicated ALB derivatives (50 µM). Calcium responses were recorded as described. Data shown are mean values±standard deviation derived from duplicates relative to peak calcium responses after treatment with agonists only (100%). B) ALB derivatives abrogate CXCL12 binding to CXCR4. CXCR4 expressing HEK293 cells were treated with Texas Red labeled CXCL12 (CXCL12-Tr) in the presence or absence of ALB peptides. Real-time fluorescence monitoring of ligand-receptor interactions was carried out as described. Shown are bound CXCL12-Tr levels in the presence of ALB peptides relative to CXCL12-Tr only treated cells (100% bound). Values were derived from a duplicate experiment.

---

The invention claimed is:

1. An isolated, purified, recombinant, or synthetic peptide wherein the peptide is
   a) an amino acid sequence selected from the group consisting of SEQ ID NO: 9-14, 20, 21, and 29, or
   b) an amidated, acetylated, sulfated, phosphorylated, or glycosylated derivative of an amino acid sequence selected from the group consisting of SEQ ID NO: 9-14, 20, 21, and 29.

2. The peptide according to claim 1 wherein the peptide is the amidated, acetylated, sulfated, phosphorylated, or glycosylated derivative of an amino acid sequence selected from the group consisting of SEQ ID NO: 9-14, 20, 21, and 29.

3. The peptide according to claim 1 wherein the peptide is the amino acid sequence selected from the group consisting of SEQ ID NO: 9-14, 20, 21, and 29.

4. A vector incorporating a polynucleotide coding for the peptide according to claim 1.

5. A genetically engineered host cell incorporating the vector according to claim 4.

6. A medicament comprising the polypeptide according to claim 1 and a medicinally compatible carrier in a galenic formulation.

7. A diagnostic agent comprising in combination with a compatible carrier a polynucleotide coding for the peptide according to claim 1.

8. The medicament of claim 6 in a galenic formulation for oral, intravenous, intramuscular, intracutaneous, subcutaneous, or intrathecal administration or in an aerosol form for transpulmonary administration.

9. A method comprising administering to a patient in need thereof an effective amount of the peptide according to claim 1 for the treatment of HIV-1 or HIV-2.

* * * * *

UNITED STATES PATENT AND TRADEMARK OFFICE
CERTIFICATE OF CORRECTION

PATENT NO. : 9,045,563 B2
APPLICATION NO. : 12/452480
DATED : June 2, 2015
INVENTOR(S) : Wolf-Georg Forssmann et al.

Page 1 of 1

It is certified that error appears in the above-identified patent and that said Letters Patent is hereby corrected as shown below:

ON THE TITLE PAGE

Assignee:

change "PHARIS BIOTECH GMBH" to --PHARIS BIOTEC GMBH--.

Signed and Sealed this
Twenty-third Day of February, 2016

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 9,045,563 B2 |
| APPLICATION NO. | : 12/452480 |
| DATED | : June 2, 2015 |
| INVENTOR(S) | : Wolf-Georg Forssmann |

Page 1 of 1

It is certified that error appears in the above-identified patent and that said Letters Patent is hereby corrected as shown below:

ON THE TITLE PAGE

"Assignee:

change "PHARIS BIOTECH GMBH" to --PHARIS BIOTEC GMBH--."
(as corrected to read in the Certificate of Correction issued February 23, 2016) is deleted and patent is returned to its original state with the applicant & assignee name in patent to read
-- (73)   Assignee: PHARIS BIOTECH GMBH, Hannover
        (DE) --

Signed and Sealed this
Seventh Day of June, 2016

Michelle K. Lee
*Director of the United States Patent and Trademark Office*

SEQUENCE LISTING

```
<160> NUMBER OF SEQ ID NOS: 32

<210> SEQ ID NO 1
<211> LENGTH: 9
<212> TYPE: PRT
<213> ORGANISM: Homo sapiens

<400> SEQUENCE: 1

Val Pro Gln Val Ser Thr Pro Thr Leu
1               5

<210> SEQ ID NO 2
<211> LENGTH: 10
```

```
<212> TYPE: PRT
<213> ORGANISM: Homo sapiens

<400> SEQUENCE: 2

Lys Val Pro Gln Val Ser Thr Pro Thr Leu
1               5                   10

<210> SEQ ID NO 3
<211> LENGTH: 11
<212> TYPE: PRT
<213> ORGANISM: Homo sapiens

<400> SEQUENCE: 3

Lys Lys Val Pro Gln Val Ser Thr Pro Thr Leu
1               5                   10

<210> SEQ ID NO 4
<211> LENGTH: 12
<212> TYPE: PRT
<213> ORGANISM: Homo sapiens

<400> SEQUENCE: 4

Thr Lys Lys Val Pro Gln Val Ser Thr Pro Thr Leu
1               5                   10

<210> SEQ ID NO 5
<211> LENGTH: 13
<212> TYPE: PRT
<213> ORGANISM: Homo sapiens

<400> SEQUENCE: 5

Tyr Thr Lys Lys Val Pro Gln Val Ser Thr Pro Thr Leu
1               5                   10

<210> SEQ ID NO 6
<211> LENGTH: 14
<212> TYPE: PRT
<213> ORGANISM: Homo sapiens

<400> SEQUENCE: 6

Arg Tyr Thr Lys Lys Val Pro Gln Val Ser Thr Pro Thr Leu
1               5                   10

<210> SEQ ID NO 7
<211> LENGTH: 15
<212> TYPE: PRT
<213> ORGANISM: Homo sapiens

<400> SEQUENCE: 7

Val Arg Tyr Thr Lys Lys Val Pro Gln Val Ser Thr Pro Thr Leu
1               5                   10                  15

<210> SEQ ID NO 8
<211> LENGTH: 16
<212> TYPE: PRT
<213> ORGANISM: Homo sapiens

<400> SEQUENCE: 8

Leu Val Arg Tyr Thr Lys Lys Val Pro Gln Val Ser Thr Pro Thr Leu
1               5                   10                  15

<210> SEQ ID NO 9
<211> LENGTH: 15
<212> TYPE: PRT
<213> ORGANISM: Homo sapiens
```

```
<400> SEQUENCE: 9

Leu Val Arg Tyr Thr Lys Lys Val Pro Gln Val Ser Thr Pro Thr
1               5                   10                  15

<210> SEQ ID NO 10
<211> LENGTH: 14
<212> TYPE: PRT
<213> ORGANISM: Homo sapiens

<400> SEQUENCE: 10

Leu Val Arg Tyr Thr Lys Lys Val Pro Gln Val Ser Thr Pro
1               5                   10

<210> SEQ ID NO 11
<211> LENGTH: 13
<212> TYPE: PRT
<213> ORGANISM: Homo sapiens

<400> SEQUENCE: 11

Leu Val Arg Tyr Thr Lys Lys Val Pro Gln Val Ser Thr
1               5                   10

<210> SEQ ID NO 12
<211> LENGTH: 12
<212> TYPE: PRT
<213> ORGANISM: Homo sapiens

<400> SEQUENCE: 12

Leu Val Arg Tyr Thr Lys Lys Val Pro Gln Val Ser
1               5                   10

<210> SEQ ID NO 13
<211> LENGTH: 11
<212> TYPE: PRT
<213> ORGANISM: Homo sapiens

<400> SEQUENCE: 13

Leu Val Arg Tyr Thr Lys Lys Val Pro Gln Val
1               5                   10

<210> SEQ ID NO 14
<211> LENGTH: 10
<212> TYPE: PRT
<213> ORGANISM: Homo sapiens

<400> SEQUENCE: 14

Leu Val Arg Tyr Thr Lys Lys Val Pro Gln
1               5                   10

<210> SEQ ID NO 15
<211> LENGTH: 9
<212> TYPE: PRT
<213> ORGANISM: Homo sapiens

<400> SEQUENCE: 15

Leu Val Arg Tyr Thr Lys Lys Val Pro
1               5

<210> SEQ ID NO 16
<211> LENGTH: 8
<212> TYPE: PRT
<213> ORGANISM: Homo sapiens

<400> SEQUENCE: 16
```

```
Leu Val Arg Tyr Thr Lys Lys Val
1               5

<210> SEQ ID NO 17
<211> LENGTH: 7
<212> TYPE: PRT
<213> ORGANISM: Homo sapiens

<400> SEQUENCE: 17

Leu Val Arg Tyr Thr Lys Lys
1               5

<210> SEQ ID NO 18
<211> LENGTH: 6
<212> TYPE: PRT
<213> ORGANISM: Homo sapiens

<400> SEQUENCE: 18

Leu Val Arg Tyr Thr Lys
1               5

<210> SEQ ID NO 19
<211> LENGTH: 8
<212> TYPE: PRT
<213> ORGANISM: Homo sapiens

<400> SEQUENCE: 19

Leu Leu Val Arg Tyr Thr Lys Lys
1               5

<210> SEQ ID NO 20
<211> LENGTH: 13
<212> TYPE: PRT
<213> ORGANISM: Homo sapiens

<400> SEQUENCE: 20

Leu Leu Val Arg Tyr Thr Lys Lys Val Pro Gln Val Ser
1               5                   10

<210> SEQ ID NO 21
<211> LENGTH: 12
<212> TYPE: PRT
<213> ORGANISM: Homo sapiens

<400> SEQUENCE: 21

Ile Val Arg Tyr Thr Lys Lys Val Pro Gln Val Ser
1               5                   10

<210> SEQ ID NO 22
<211> LENGTH: 12
<212> TYPE: PRT
<213> ORGANISM: Homo sapiens

<400> SEQUENCE: 22

Phe Val Arg Tyr Thr Lys Lys Val Pro Gln Val Ser
1               5                   10

<210> SEQ ID NO 23
<211> LENGTH: 12
<212> TYPE: PRT
<213> ORGANISM: Homo sapiens

<400> SEQUENCE: 23

Ala Val Arg Tyr Thr Lys Lys Val Pro Gln Val Ser
```

<210> SEQ ID NO 24
<211> LENGTH: 12
<212> TYPE: PRT
<213> ORGANISM: Homo sapiens

<400> SEQUENCE: 24

Gly Val Arg Tyr Thr Lys Lys Val Pro Gln Val Ser
1               5                   10

<210> SEQ ID NO 25
<211> LENGTH: 8
<212> TYPE: PRT
<213> ORGANISM: Homo sapiens

<400> SEQUENCE: 25

Leu Val Arg Tyr Thr Lys Lys Val
1               5

<210> SEQ ID NO 26
<211> LENGTH: 8
<212> TYPE: PRT
<213> ORGANISM: Homo sapiens

<400> SEQUENCE: 26

Leu Val Arg Tyr Thr Lys Lys Ala
1               5

<210> SEQ ID NO 27
<211> LENGTH: 8
<212> TYPE: PRT
<213> ORGANISM: Homo sapiens

<400> SEQUENCE: 27

Leu Val Arg Tyr Thr Lys Ala Val
1               5

<210> SEQ ID NO 28
<211> LENGTH: 8
<212> TYPE: PRT
<213> ORGANISM: Homo sapiens

<400> SEQUENCE: 28

Leu Val Arg Tyr Thr Ala Lys Val
1               5

<210> SEQ ID NO 29
<211> LENGTH: 8
<212> TYPE: PRT
<213> ORGANISM: Homo sapiens

<400> SEQUENCE: 29

Leu Val Arg Tyr Ala Lys Lys Val
1               5

<210> SEQ ID NO 30
<211> LENGTH: 8
<212> TYPE: PRT
<213> ORGANISM: Homo sapiens

<400> SEQUENCE: 30

Leu Val Arg Ala Thr Lys Lys Val
1               5

```
<210> SEQ ID NO 31
<211> LENGTH: 8
<212> TYPE: PRT
<213> ORGANISM: Homo sapiens

<400> SEQUENCE: 31

Leu Val Ala Tyr Thr Lys Lys Val
1               5

<210> SEQ ID NO 32
<211> LENGTH: 8
<212> TYPE: PRT
<213> ORGANISM: Homo sapiens

<400> SEQUENCE: 32

Leu Ala Arg Tyr Thr Lys Lys Val
1               5
```